United States Patent [19]

Parekh et al.

[11] Patent Number: 5,667,984
[45] Date of Patent: Sep. 16, 1997

[54] SEQUENCING OF OLIGOSACCHARIDES

[75] Inventors: Rajesh B. Parekh, Oxford; Sally B. Prime, Oxon, both of United Kingdom

[73] Assignee: Oxford Glycosystems Ltd., Abington, United Kingdom

[21] Appl. No.: 140,144

[22] PCT Filed: May 7, 1992

[86] PCT No.: PCT/GB92/00829

§ 371 Date: Dec. 8, 1993

§ 102(e) Date: Dec. 8, 1993

[87] PCT Pub. No.: WO92/19768

PCT Pub. Date: Nov. 12, 1992

[30] Foreign Application Priority Data

May 7, 1991 [GB] United Kingdom ............... 9109853
Oct. 29, 1991 [GB] United Kingdom ............... 9122865

[51] Int. Cl.$^6$ ............... C12Q 1/34; C12Q 1/40; C12Q 1/54; C12Q 1/26
[52] U.S. Cl. ............... 435/18; 435/22; 435/16; 435/15; 435/13; 435/7.4; 435/7.1; 435/14; 435/25
[58] Field of Search ............... 435/18, 4, 16, 435/819, 15, 7.4, 13, 97, 288, 22, 7.1, 14, 25; 424/101; 436/534

[56] References Cited

U.S. PATENT DOCUMENTS

| | | | |
|---|---|---|---|
| 4,240,751 | 12/1980 | Linnecke et al. | 435/808 |
| 4,243,753 | 1/1981 | Regnier et al. | 435/4 |
| 4,250,394 | 2/1981 | O'Connor | 436/534 |
| 4,859,581 | 8/1989 | Nicolson et al. | 435/13 |
| 5,100,778 | 3/1992 | Rademacher et al. | 435/18 |
| 5,180,674 | 1/1993 | Roth | 435/819 |
| 5,284,558 | 2/1994 | Lindhardt et al. | 435/18 |

FOREIGN PATENT DOCUMENTS 0 421 972 A2  10/1990  European Pat. Off..
92/02816  2/1992  WIPO.

OTHER PUBLICATIONS

Joseph K. Welply; "Sequencing methods for carbohydrates and their biological applications"; *TIBTECH;* 7 (1989) January; pp. 5–10.

Martin F. Chaplin; "A Rapid and Sensitive Method for the Analysis of Carbohydrate Components in Glycoproteins Using Gas–Liquid Chromatography"; *Analytical Biochemistry;* 1982; pp. 336–341.

Hardy, Mark R., "Monosaccharide Analysis of Glycoconjugates by High–Performance Anion–Exchange Chromatography with Pulsed Amperometric Detection," *Methods in Enzymology,* vol. 179, pp. 76–83 (1989).

Pipkorn et al, Int. J. Peptide Protein Res., 27, 1986, pp. 583–588.

*Primary Examiner*—John Kight
*Assistant Examiner*—Louise Leary
*Attorney, Agent, or Firm*—Oliff & Berridge

[57] ABSTRACT

A process suitable for use in the sequencing of an oligosaccharide compound includes a first analysis of a primary oligosaccharide compound's monosaccharide composition, selection of sequencing agents to apply to the oligosaccharide compound, applying a selected sequencing agent to the oligosaccharide compound, and analyzing a released monosaccharide to select a second sequencing agent. The sequencing agent may be, for example, an enzyme. The oligosaccharide compound may be, for example, an oligosaccharide, or a product of an oligosaccharide, or a species having an oligosaccharide portion.

11 Claims, 20 Drawing Sheets

SEQUENCING OF OLIGOSACCHARIDES

The present invention relates to the analysis of oligosaccharides and more particularly to the form of analysis known as sequencing of oligosaccharides.

According to one aspect of the present invention there is provided apparatus suitable for use in the sequencing of an oligosaccharide which apparatus includes means for selecting a sequencing agent to be applied to an oligosaccharide entity.

According to another aspect of the present invention there is provided a process suitable for use in the sequencing of an oligosaccharide which process includes the use of a means for selecting a sequencing agent to be applied to an oligosaccharide entity.

The oligosaccharide entity may be, for example, an oligosaccharide, or a product of an oligosaccharide, or a species having an oligosaccharide portion. A product of an oligosaccharide may be, for example, a product produced by previously applying a sequencing agent to an oligosaccharide; by way of example, the product may itself be an oligosaccharide.

Oligosaccharides form a class of chemical compounds which are each made up of a number of monosaccharide units linked together by glycosidic bonds. Important sources of naturally occurring oligosaccharides are glycoproteins in which saccharides are found linked to a peptide chain either by an N-glycosidic bond or by an O-glycosidic bond; these oligosaccharides may vary from a few monosaccharide units to highly branched structures containing many (e.g. over 30) monosaccharide units.

The "sequencing" of an oligosaccharide involves deducing certain information concerning the structure of the oligosaccharide such as (i) the type of each monosaccharide unit in the oligosaccharide, (ii) the order in which the monosaccharide units are arranged in the oligosaccharide, (iii) the position of linkages between each of the monosaccharide units (e.g. 1–3, 1–4, etc.), and hence any branching pattern and/or (iv) the orientation of linkage between each of the monosaccharide units (i.e. whether a linkage is an $\alpha$ linkage or a $\beta$ linkage).

Where it is desired to obtain as much information as possible regarding the structure of an oligosaccharide then "sequencing" of the oligosaccharide may be carried out to obtain as much information as possible in relation to features (i) to (iv) inclusively immediately hereinbefore disclosed.

An agent which assists in obtaining information in relation to some or all of features (i) to (iv) inclusively on being applied to an oligosaccharide entity may be regarded as a "sequencing agent". By way of example, a sequencing agent may be a physical agent or a chemical agent. Examples of physical sequencing agents are proton n.m.r., carbon-13 n.m.r. and mass spectrometry for molecular weight determinations.

Also, by way of example, a sequencing agent may be capable of causing cleavage of a chemical bond or capable of causing formation of a chemical bond.

Where, for example, a sequencing agent is a chemical reagent (which may be, for example, a chemical reagent or a biochemical reagent) the sequencing agent may be regarded as a sequencing reagent. Examples of sequencing reagents are enzymes (such as exoglycosidases and endoglycosidases) and chemical reagents (e.g. a periodate) capable of effecting chemical cleavage of an oligosaccharide and/or a chemical modification of an oligosaccharide which assists in obtaining information regarding the structure of the oligosaccharide as hereinbefore disclosed.

As hereinbefore disclosed the oligosaccharide entity may be, for example, an oligosaccharide, or a product of an oligosaccharide, or a species having an oligosaccharide portion.

Thus, it is to be understood that, by way of example, an oligosaccharide as such may be subjected to sequencing in accordance with the present invention; by way of further example, as an alternative, a product of an oligosaccharide may be subjected to sequencing in accordance with the present invention. (It will be appreciated that the product may itself be an oligosaccharide.)

Alternatively, for example, an oligosaccharide provided as an oligosaccharide portion of a species having an oligosaccharide portion (e.g. an oligosaccharide linked to a conjugate) may be subjected to sequencing in accordance with the present invention. Glycoproteins and glycolipids are examples of species having a portion comprising an oligosaccharide which may be subjected to sequencing in accordance with the present invention such that oligosaccharide is subjected to sequencing.

Thus, by way of further example, an oligosaccharide may, if desired, be subjected to sequencing in accordance with the present invention whilst still attached to a conjugate thereof (e.g. a peptide chain) provided that the conjugate does not interfere in the sequencing to any unacceptable degree.

From the foregoing disclosure it will be appreciated that, by way of example, an oligosaccharide to be subjected to sequencing may be provided in any suitable form and in any suitable manner.

Also, from the foregoing disclosure it will be appreciated that in accordance with the present invention sequencing of an oligosaccharide may include, for example, applying a sequencing agent to an oligosaccharide, or a product thereof, or a species having an oligosaccharide portion.

Examples of enzymes which may be used as sequencing reagents are given in Table I.

In Table I there is presented a list of enzymes commonly used for cleaving monosaccharides from N-linked oligosaccharides and the rules showing which monosaccharides are cleaved by each of these enzymes and from which part of an oligosaccharide structure cleavage can be expected.

A sequencing agent which is capable of bringing about a cleaving of a particular linkage or linkages in an oligosaccharide may be an agent capable of effecting a specific transformation on the oligosaccharide.

It will be appreciated that a sequencing agent may be chosen such that the reaction products obtained when it is applied to the oligosaccharide entity (e.g. contacted with the oligosaccharide entity in the case of a chemical or biochemical reagent) will reveal the presence or absence of a particular structural sub-unit (e.g. a monosaccharide unit) in the oligosaccharide entity.

TABLE I

| Enzyme | Monosaccharide Cleaved | Rules for Cleavage |
|---|---|---|
| 1) Achatina fulica beta mannosidase | Mannose | 1-beta-4 to any site |
| 2) A. saitoi alpha mannosidase | Mannose | 1-alpha-2 to any site |
| 3) Jack bean alpha mannosidase | Mannose | (i) mannose 1-alpha-2 to any site (ii) cleaves the 1-alpha-3,6 mannoses if there is no bisect on the middle mannose |

TABLE I-continued

| Enzyme | Monosaccharide Cleaved | Rules for Cleavage |
|---|---|---|
| 4) Jack bean alpha mannosidase (under arm-specific conditions) | Mannose | Different from 3) in that it will not cleave the mannose 1-alpha-6 case when restricted by a side arm longer than 1 unit out from the middle mannose |
| 5) Bovine testis beta galactosidase | Galactose | 1-beta-3,4 to any non-branched site |
| 6) Jack bean beta galactosidase | Galactose | 1-beta-4 to any non-branched site |
| 7) C. lampas beta xylosidase | Xylose | 1-beta-any to any site |
| 8) S. pneum beta N-acetyl hexosaminidase | N-acetyl hexosamine | (i) 1-beta-3 to any non-branched site (ii) 1-beta-2 mannose 1-alpha-3 or 6 to middle mannose provided the first mannose does not have a bond at atom 6, and also in the case of 1-alpha-6, that the middle mannose is not bisected |
| 9) Jack bean beta N-acetyl hexosaminidase | N-acetyl hexosamine | 1-beta-any to any site |
| 10) Bovine epididymis alpha fucosidase | Fucose | 1-alpha-3,4,6 to any site |
| 11) C. lampas alpha fucosidase | Fucose | 1-alpha-2,3,4,6 to any site |
| 12) Coffee bean alpha galactosidase | Galactose | 1-alpha-3,6 to any non-branched site |
| 13) Almond alpha fucosidase | Fucose | 1-alpha-3,4 to any site |

Thus, in one embodiment of the present invention there is provided a process for the sequencing of an oligosaccharide which process includes applying a sequencing agent to an oligosaccharide entity and analysing for a component of the oligosaccharide entity, which component has been released from the oligosaccharide entity by means of the sequencing agent.

It will be appreciated that in accordance with the immediately foregoing embodiment of the present invention it is not the oligosaccharide entity which is analysed after application of the sequencing agent to obtain information regarding the structure of the oligosaccharide entity. Rather, in accordance with the immediately foregoing embodiment of the present invention, it is a component which is released or cleaved from an oligosaccharide entity that is analysed for in order to facilitate "sequencing".

Thus, for example, when analysis is carried out, the detection of a component comprising a particular monosaccharide in the products of a cleaving reaction may be used to confirm the presence of a particular linkage and monosaccharide in the original oligosaccharide structure of the oligosaccharide entity.

In another embodiment of the present invention there is provided apparatus which includes means for selecting a sequencing agent to be applied to an oligosaccharide entity and analysing means for analysing for a component of the oligosaccharide entity, which component has been released from the oligosaccharide entity by means of a sequencing agent.

A set of possible structures for an oligosaccharide (i.e. a set of "candidate" structures) may be prepared in any suitable way.

For example, a set of "candidate" structures may be drawn up from literature surveys.

By way of further example, a set of "candidate" structures may be prepared by considering possible permutations of putting together monosaccharide units.

Alternatively, by way of further example, a concept of structures and sub-structures may be used (as discussed further hereinafter) to prepare a set of candidate structures for an unknown oligosaccharide.

It will also be appreciated that, for example, by sequentially applying different sequencing agents to an oligosaccharide entity and analysing the products obtained by use of each sequencing agent it is possible to eliminate certain structures from consideration (i.e. eliminate certain structures from a postulated set of possible "candidate" structures for the oligosaccharide entity) and to confirm the presence of a certain structure or certain structures thereby enabling information regarding the structure of the oligosaccharide entity to be deduced.

Thus, for example, by sequentially applying different sequencing agents either to a given oligosaccharide entity, comprising an oligosaccharide, or to a product thereof (being a product produced by previously applying a sequencing agent to the oligosaccharide), or to a species having an oligosaccharide portion, and analysing the products obtained by use of each sequencing agent it is possible to eliminate certain structures from consideration (i.e. eliminate certain structures from a postulated set of possible "candidate" structures for the oligosaccharide) and to confirm the presence of a certain structure or certain structures thereby enabling information regarding the structure of the oligosaccharide (which may be, for example, an oligosaccharide as such or an oligosaccharide portion of a species having an oligosaccharide portion) to be deduced.

The presence and linkage of a particular monosaccharide at an end of an oligosaccharide structure of an oligosaccharide entity may be determined, for example, by the ability of a given sequencing agent (e.g. a biochemical reagent such as an enzyme (e.g. an exoglycosidase)) to cause cleavage of that linkage; thus, if cleavage occurs, then detection of the particular monosaccharide in the reaction products of the cleaving reaction will confirm the presence of that linkage in the original oligosaccharide structure. Thus, by sequentially using a plurality of different sequencing agents having known specific linkage cleaving capabilities it is possible to deduce increasing amounts of information regarding the structure of the oligosaccharide entity under analysis. It is to be understood that where no single sequencing agent can be found which can distinguish between candidate oligosaccharide structures then consideration may be given to possible combinations of two, three or more agents to be applied one after the other; at each stage of consideration an agent which has no effect on any of a set of candidate structures may be eliminated. Consideration may also be given to using a combination of two or more agents simultaneously as this may lead to a reduction in the time required to carry out a sequencing analysis.

Thus, an iterative process may be used whereby a cycle of analysis, application of a sequencing agent (or a combination of sequencing agents) and subsequent analysis is repeated until as much information as possible has been obtained regarding the structure of an oligosaccharide entity with the agents available or the sample of oligosaccharide entity is exhausted.

From the foregoing it will be appreciated that in certain circumstances a particular sequencing agent may be such that it does not react with the oligosaccharide entity to give products thereby permitting the fact that it did not so react to allow deductions to be made regarding the structure of the oligosaccharide entity.

The effectiveness of the sequencing of an oligosaccharide entity may be seen as depending upon the choice of sequencing agent to be applied at various stages in sequencing and the accuracy of interpretation of the results of applying a given sequencing agent to an oligosaccharide entity.

To a large degree, a good choice of sequencing agent depends upon the skill of an experienced operator who has already made some intelligent guesses about the type of oligosaccharide structure being investigated.

A poor choice of sequencing agent may result in little or no additional information being revealed by a particular application of a sequencing agent and thus lead to a waste of time and materials. Also there is present the danger that prejudices of an operator will mask ambiguities in the interpretation of results; for example, an operator may assign a single structure which is consistent with experimental results, whereas in reality there may be more than one structure consistent with the same experimental results.

A further difficulty may arise in defining the point in sequencing at which no further information can be revealed by the use of available sequencing agents.

For oligosaccharide entities (e.g. oligosaccharides) obtained from glycoproteins the sequencing thereof may be assisted by a knowledge of the biosynthetic pathways involved in building up oligosaccharide structures. Thus, for example, for N-linked oligosaccharides it is known that there is a characteristic core structure and that additional monosaccharides may only add on in certain well defined orders and branching patterns.

This knowledge may be used to develop for oligosaccharides a concept of structures and sub-structures; this is discussed further hereinafter with reference to FIGS. 1, 2, and 3 of the accompanying drawings.

For example, if an oligosaccharide entity to be subjected to sequencing in accordance with the present invention is an oligosaccharide which has been obtained from a mixture of oligosaccharides released from a glycoprotein by the enzyme peptide-N-glycosidase F, it may be assumed that the oligosaccharide is an N-glycan and that the structure thereof is likely to be a structure similar to those of FIG. 1, FIG. 2 or FIG. 3 of the accompanying drawings or a sub-structure generated from the structures similar to those of FIGS. 1, 2 and 3 of the accompanying drawings.

In one embodiment of an apparatus in accordance with the present invention an apparatus includes means for applying a sequencing agent to an oligosaccharide entity, analysing means for analysing products obtained by applying the sequencing agent to an oligosaccharide entity, means for selecting a sequencing agent to be applied to an oligosaccharide entity, and means for feeding analysis results from the analysing means to the means for selecting a sequencing agent to be applied to an oligosaccharide entity.

In another embodiment of apparatus in accordance with the present invention an apparatus includes all of the features of the apparatus immediately hereinbefore disclosed in the immediately preceding paragraph and additionally includes means for applying to an oligosaccharide entity, a sequencing agent as selected by the means for selecting a sequencing agent.

Apparatus in accordance with the present invention may also include a means for carrying out a preliminary analysis of an oligosaccharide entity; it will be appreciated that this means optionally may be, or may be part of, the analysing means for analysing products obtained by applying the sequencing agent to an oligosaccharide entity. Thus, it is to be understood that, if desired, the analysing means may be one capable of detecting monosaccharide units from an oligosaccharide entity.

The apparatus may also, optionally, include means for feeding the results of a preliminary analysis to the means for selecting a sequencing agent to be applied to an oligosaccharide entity.

The means for applying the sequencing agent to an oligosaccharide entity may comprise, for example, a means for contacting together a sequencing agent and an oligosaccharide entity (e.g. a reaction vessel).

Also, the apparatus may include, for example, means for supplying a sequencing agent to a means for contacting together a sequencing agent and an oligosaccharide entity.

The means for supplying a sequencing agent may be, for example, such that a plurality of sequencing agents may be supplied individually or may be, for example, such that sequencing agents may be supplied in a selected sequence or combination.

A sequencing agent, or a combination of sequencing agents, may be applied to an oligosaccharide entity in a suitable manner.

The sequencing agent or a combination of sequencing agents may be introduced in a suitable solvent to a means for contacting together a sequencing agent and an oligosaccharide entity.

Optionally, for example, an oligosaccharide entity, to be subjected to sequencing may be immobilised on a suitable support material.

Thus, for example, an apparatus in accordance with the present invention may include a support material upon which may be immobilised an oligosaccharide entity, to be subjected to sequencing.

Also, for example, a process in accordance with the present invention may include the step of immobilising upon a support material an oligosaccharide entity, to be subjected to sequencing.

The oligosaccharide entity may, for example, be immobilised on a support material by any suitable means. Thus, where, for example, the oligosaccharide entity is an oligosaccharide or a product thereof immobilisation may be effected, for example, by means of chemical attachment (e.g. covalent linkage) via a reducing terminus of an oligosaccharide.

An oligosaccharide entity comprising an oligosaccharide, or a product thereof, may be immobilised in accordance with the present invention for example by direct covalent linkage with a support material, or by direct non-covalent (e.g. hydrophilic) linkage with a support material.

Alternatively, by way of example, an oligosaccharide entity comprising a species having an oligosaccharide portion may be immobilised on a support material before being subjected to sequencing.

By way of example, where it is desired to immobilise an oligosaccharide, or a product thereof, whilst still attached to a conjugate the conjugate may be linked to a support material (e.g. by covalent linkage or non-covalent (e.g. hydrophilic) linkage) such that the oligosaccharide, or product thereof, is indirectly linked to the support material via the conjugate.

Where an oligosaccharide entity is immobilised on a support material the oligosaccharide entity, or any product thereof produced by application of the sequencing agent and retained on the support material, may be readily separated from released products, such as species (with new reducing termini), generated by the application of a sequencing agent or agents. Thus, for example, the product of the oligosaccharide entity may be retained on the support material and species with new reducing termini may be removed by suitable washing.

An example of a support material for use in accordance with the present invention is a solid support material comprising 1,1'carbonyldiimidazole activated agarose.

Immobilisation of an oligosaccharide entity on a support material may be effected by any suitable means. Thus, for example, where the oligosaccharide entity is an oligosaccharide, or a product of an oligosaccharide, immobilisation of an oligosaccharide, or a product of an oligosaccharide, on a support material may be effected by the following procedure:

unreduced oligosaccharide+2-amino pyridine/ $NaBH_3CN \rightarrow$ oligo-pyridylamino derivative→conjugation.

By way of further example, where an oligosaccharide entity is an oligosaccharide or a product of an oligosaccharide, the oligosaccharide or product thereof may be immobilised on a support material by means of the following procedure:

unreduced oligosaccharide+dansyl hydrazine/ TFA→oligo-dansyl hydrazine derivative, oligo-dansyl hydrazine derivative+$NaBH_4$/ $H_2O$→conjugation.

It is to be understood that attachment of an oligosaccharide entity, via a reducing terminus, to a support material, is preferably independent of any oligosaccharide structure present in the oligosaccharide entity; the attachment may not, for example, require a reducing terminus monosaccharide to be retained in a ring-closed configuration.

Apparatus in accordance with the present invention may include, for example, a filtration means (e.g. a filtration column involving chromatographic separation or other chemical separation means) to permit removal of excess sequencing agent or agents from a reaction mixture (e.g. formed in a reaction vessel) prior to using an analysing means.

An analysing means for use in accordance with the present invention may include a detector capable of measuring the types and relative amounts of monosaccharides present in an oligosaccharide and/or monosaccharides produced by applying a sequencing agent to an oligosaccharide entity, (e.g. by bringing together a sequencing agent and an oligosaccharide entity). By way of example, the monosaccharides may be measured as monosaccharides or as derivatised products thereof.

Apparatus in accordance with the present invention may also, for example, include a flushing means whereby excess sequencing agent may be removed from a means for contacting together a sequencing agent and an oligosaccharide entity (e.g. a reaction vessel) prior to the introduction of a further sequencing agent.

A means for contacting together a sequencing agent and an oligosaccharide entity may be, for example, supplied with means for maintaining a controlled temperature.

It has been hereinbefore disclosed that an oligosaccharide entity to be subjected to analysis in accordance with the present invention may, for example, be immobilised on a suitable support material. However, by way of further example, an oligosaccharide entity may be subjected to analysis in accordance with the present invention without such immobilisation; thus, for example, an oligosaccharide entity may have applied thereto a sequencing agent, or a sequence or a plurality of sequencing agents, whilst in free solution.

In apparatus in accordance with the present invention the means for selecting a sequencing agent to be applied to an oligosaccharide entity, may be, for example, a unit capable of making logical choices (e.g. a logic unit).

Also, the unit may be such that it is capable of interpreting results generated by the analysing means and capable of selecting a sequencing agent (or a combination of sequencing agents) to be applied to an oligosaccharide entity. Thus, for example, the unit may be such as to be capable of requesting the application of a sequencing agent (or a combination of sequencing agents) to an oligosaccharide entity, the application of another sequencing agent (or combination of sequencing agents) to an oligosaccharide entity being a product of an oligosaccharide entity or the application of another or a further sequencing agent (or combination of sequencing agents) to an oligosaccharide entity, or to an oligosaccharide entity being a product of an oligosaccharide entity.

It is to be understood that, by way of example, an apparatus in accordance with the present invention may be such that, in operation, a unit as hereinbefore disclosed controls application of a sequencing agent or agents to an oligosaccharide entity to be analysed (in immobilised form or otherwise), and interprets the output from a detector such as to provide a fully automated apparatus for the identification and sequencing of an unknown oligosaccharide structure of an oligosaccharide entity.

Thus, for example, an apparatus in accordance with the present invention may be such that, in operation, a unit as hereinbefore disclosed controls addition of a sequencing agent or agents to a reaction vessel, containing (in immobilised form or otherwise) an oligosaccharide entity to be analysed, and interprets the output from a detector such as to provide a fully automated apparatus for the identification and sequencing of an unknown oligosaccharide structure of an oligosaccharide entity.

An apparatus in accordance with the present invention may be arranged, for example, to produce results of identification and sequencing of an oligosaccharide structure of an oligosaccharide entity in any suitable manner.

In one embodiment of a process in accordance with the present invention a process includes analysing an oligosaccharide entity, applying a sequencing agent to an oligosaccharide entity, analysing products obtained by applying the sequencing agent to an oligosaccharide entity and feeding analysis results thus obtained to a means for selecting a sequencing agent to be contacted with an oligosaccharide entity.

In another embodiment of a process in accordance with the present invention a process includes all of the steps of the process hereinbefore disclosed in the immediately preceding paragraph and also additionally includes the step of applying a sequencing agent, as selected by the means for selecting a sequencing agent, to an oligosaccharide entity.

A process in accordance with the present invention may also include the step of carrying out a preliminary analysis of the oligosaccharide entity of unknown structure prior to application of a sequencing agent.

The results of such an analysis may be fed to the means for determining a sequencing reagent.

It will be appreciated that a preliminary compositional analysis may enable the number of candidate oligosaccharide structures, that need to be considered during subsequent structural analysis, to be reduced; thus, such a preliminary structural analysis may enable the number of sequencing agent applications to be reduced.

The analysis of the oligosaccharide entity (e.g. a preliminary analysis or any subsequent analysis) may be effected in any suitable way. Thus, for example, the type and number of each monosaccharide in the oligosaccharide entity may be analysed (i.e. a compositional analysis may be effected) by any suitable method. For example, complete degradation of an oligosaccharide structure of an oligosaccharide entity into its monosaccharide components may be effected by treatment with suitable reagents (e.g. a mixture of digesting reagents such as exoglycosidases) and the resulting reaction mixture analysed using a suitable monosaccharide detection method such as those hereinafter disclosed. Alternatively, by way of further example, an oligosaccharide entity may be subjected to methanolysis, N-acetylation (if required) and silylation and the resulting substances subjected to gas chromatography/mass spectrometry.

It will be appreciated that, by way of further example, information regarding an oligosaccharide structure of an oligosaccharide entity may also be obtained by observing its retention time on a chromatographic column; by way of example the chromatographic column may be such that the retention time of an oligosaccharide entity is expressed in glucose units.

Monosaccharide detection may be effected in any suitable manner, examples of which are the following HPLC-based methods: (i) use of an SP 1010 reverse phase column, (ii) HPAE with PAD using a Dionex instrument and (iii) capillary electrophoresis.

It is to be understood that the present invention offers the possibility of optimising the use of a sequencing agent or sequencing agents, interpreting the results of an analysis of a reaction between an oligosaccharide entity and a sequencing agent unambiguously, and determining the point where no further sequencing with an available sequencing agent or agents is possible.

It will be appreciated that in accordance with the present invention it is, for example, possible to achieve a "loop" in which information obtained from a means for applying a sequencing agent to an oligosaccharide entity (or a product thereof produced by the effect of a sequencing agent upon an oligosaccharide entity) as detected by a detector is fed to a means for selecting a sequencing agent to be applied to an oligosaccharide entity (or a product thereof, produced by the effect of a sequencing agent upon the oligosaccharide entity) and the selection of sequencing agent to be next applied, as made by the means for selecting a sequencing agent, is fed to the means for applying a sequencing agent such that an iterative cycle may be established. By way of example, such an iterative cycle may be carried out in a fully automated apparatus such that a sample oligosaccharide entity may be introduced into a means for applying a sequencing agent and the apparatus allowed to function until sequencing of an oligosaccharide structure of an oligosaccharide entity ceases, or a desired degree of sequencing has taken place.

Thus, in one embodiment of the present invention there is provided an apparatus comprising a means for applying a sequencing agent to an oligosaccharide entity, means for detecting products obtained by applying the sequencing agent to an oligosaccharide entity, and means for selecting a sequencing reagent to be applied to an oligosaccharide entity, the arrangement being such that, in operation, an iterative cycle can be achieved whereby the results of applying a sequencing agent selected by the means for selecting a sequencing agent are fed back, via the means for detecting products, to the means for selecting a sequencing agent whereby the means for selecting a sequencing agent may cause a further sequencing agent to be applied to an oligosaccharide entity, or product thereof.

BRIEF DESCRIPTION OF DRAWINGS

The present invention will now be further described, by way of example only, with reference to the accompanying drawings and with reference to the Examples.

In the accompanying drawings:

In FIGS. 1, 2 and 3 of the accompanying drawings and elsewhere in this Specification the abbreviations Man, Fuc, Gal and Glcnac mean, respectively, D-mannose, L-fucose, D-galactose and N-acetyl-D-glucosamine.

Referring now to FIG. 1 of the accompanying drawings there is shown a structure for N-linked oligosaccharides of high mannose types.

It will be appreciated that the structure shows a number of mannose and N-acetyl glucosamine monosaccharide units, linked by a variety of linkages; it will also be appreciated that the N-acetyl glucosamine unit to the extreme right of the Figure may be identified as the reducing terminus of the structure. The concept of structures and sub-structures was hereinbefore disclosed and it may now be stated that it may be assumed that an oligosaccharide, for which a particular structure is relevant, is either the structure itself or is a member of a set of sub-structures of the structure, which sub-structures may be generated by performing a specific transformation on the structure. This leads to a possibility that successive sequencing of an oligosaccharide structure of an oligosaccharide entity will eliminate more and more candidate structures from a set of structures until no further information can be obtained.

Thus, an unknown oligosaccharide structure of an oligosaccharide entity may be identified as one of the structures remaining.

Figure 1:
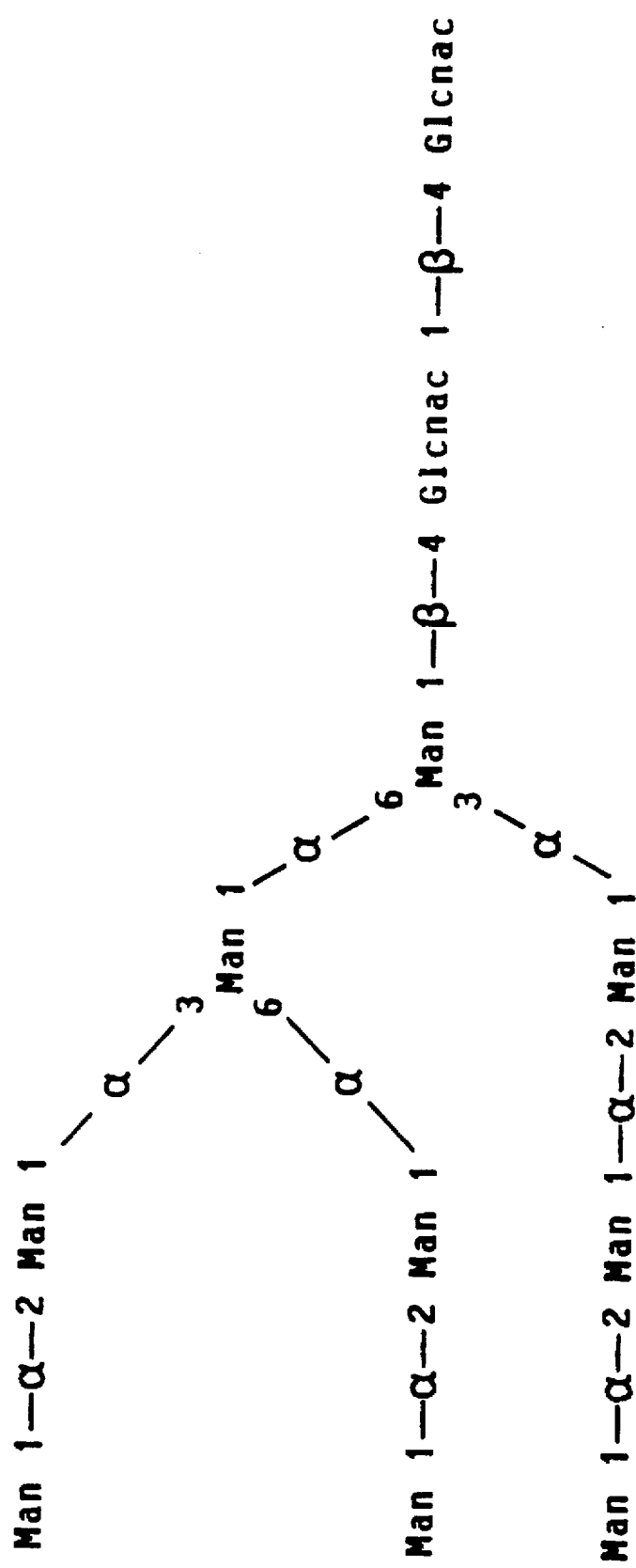
FIG. 1 shows a structure for N-linked oligosaccharides of high mannose types (Man 9)

In the case of the structure shown in FIG. 1 (and in FIGS. 2 and 3) the transformations used to generate sub-structures are successive deletions of terminal monosaccharides in all possible ways; this forms all unique sub-structures having the same root as the structure where the combination of the monosaccharides existing in the sub-structure follows that of the structure.

Figure 2:
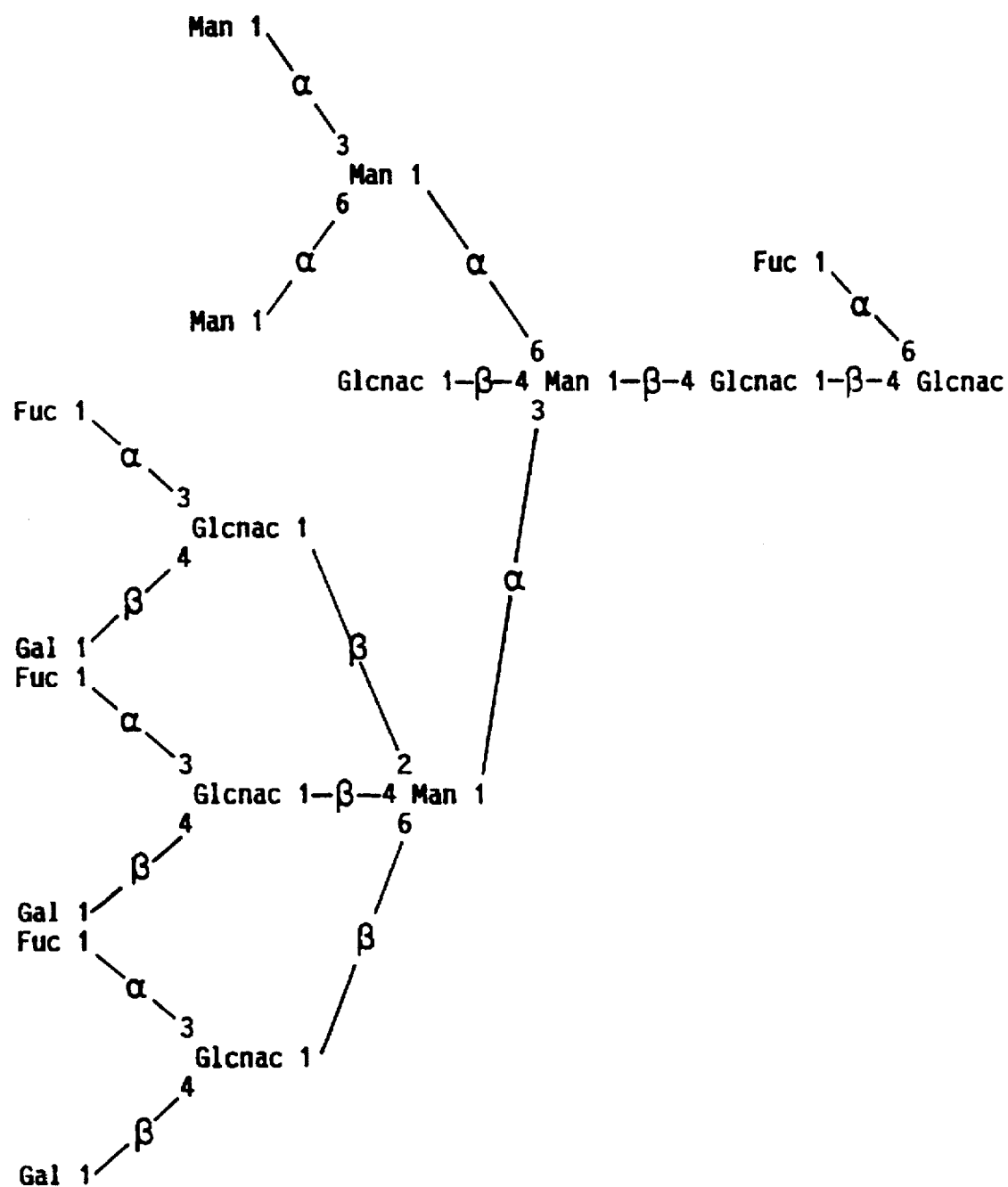
FIG. 2 shows a structure for N-linked oligosaccharides of hybrid types (Hy 2)

Referring now to FIG. 2 of the accompanying drawings there is shown a structure for N-linked oligosaccharides of hybrid types (Hy 2).

The disclosure regarding structure and sub-structures hereinbefore given in relation to FIG. 1 applies mutatis mutandis in relation to FIG. 2.

Figure 3:
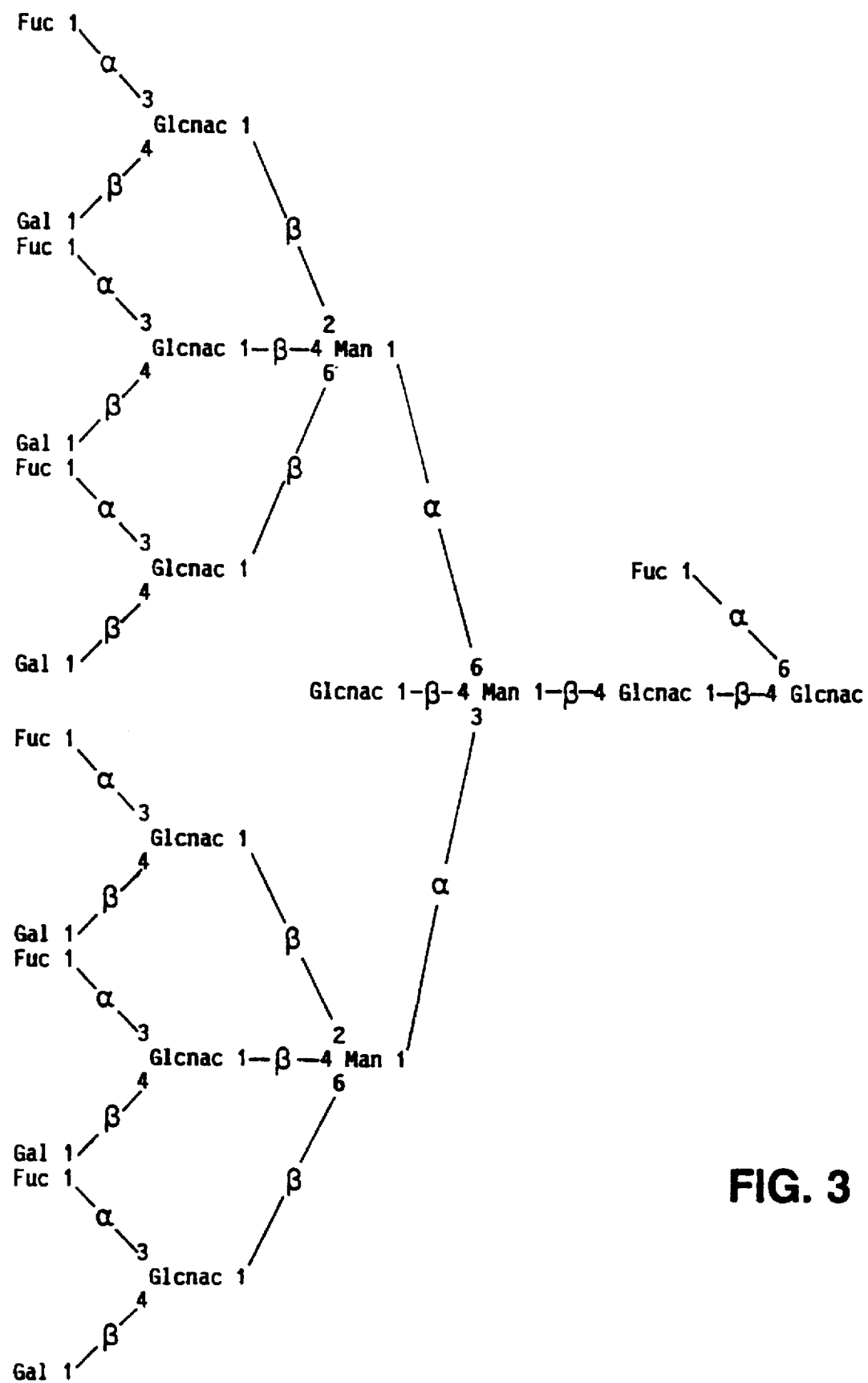
FIG. 3 shows a structure for N-linked oligosaccharides of multi-antennary types (Hex 2)

Referring now to FIG. 3 of the accompanying drawings there is shown a structure for N-linked oligosaccharides of multi-antennary types (Hex 2).

The disclosure regarding structure and substructures hereinbefore given in relation to FIG. 1 applies mutatis mutandis in relation to FIG. 3.

Figure 4:
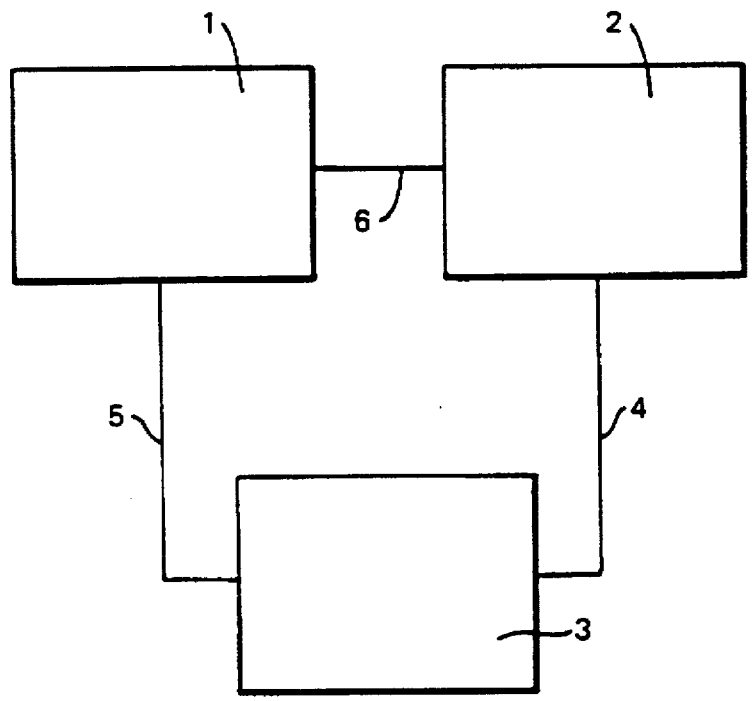
FIG. 4 shows a diagrammatic representation of an apparatus in accordance with the present invention.

Referring now to FIG. 4 of the accompanying drawings there is shown a diagrammatic representation of an apparatus in accordance with the present invention said apparatus having a means 1 for applying a sequencing agent to an oligosaccharide entity, analysing means 2 for analysing products obtained by applying the sequencing agent to an oligosaccharide entity, and means 3 for selecting a sequencing agent to be applied to an oligosaccharide entity.

In operation an oligosaccharide entity (e.g. an oligosaccharide or a product thereof, or a species having an oligosaccharide portion), is introduced into the means 1 and a first selected sequencing agent, or a first selected combination of sequencing agents, is applied. The reaction products thus obtained are analysed by means 2 and the results of the analysis passed to the means 3 via a link identified by route 4. The output of means 3 is fed back to means 1 via a link identified as route 5 whereby a second selected sequencing agent, or a second selected combination of sequencing agents, is applied to the oligosaccharide entity, or a product thereof, produced by the effect of the first selected sequencing agent, or the first selected combination of sequencing agents, upon the oligosaccharide entity.

By way of example, a third sequencing agent, or a third combination of sequencing agents, may then be applied on the basis of results obtained by applying the second sequencing agent, or second combination of sequencing agents, and so on.

Thus, it is possible to achieve a "loop" in which information obtained by applying a sequencing agent, or a combination of sequencing agents, to an oligosaccharide entity, in means 1, as detected by means 2, is fed to means 3 and the selection of sequencing agent, or agents, to be next applied, as made by means 3, is fed to means 1 such that an iterative cycle may be established. It will be appreciated that, for example, a cycle of applying a sequencing agent, analysis, and application of a further sequencing agent may be repeated until as many sequencing agents as desired have been used. Thus, for example, apparatus as hereinbefore described with reference to FIG. 4 of the accompanying drawings may be arranged to be fully automated such that a sample oligosaccharide entity may be introduced into means 1 and the apparatus allowed to function until sequencing of an oligosaccharide structure of an oligosaccharide entity ceases, or a desired degree of sequencing has taken place.

The link identified as 6 indicates that means 1 and 2 may be in communication in some suitable manner. Thus, for example, where means 2 is capable of analysis by direct optical means the link 6 may be optical. By way of further example, where means 2 is capable of analysing samples taken from means 1 the link 6 may be a means for transferring a sample from means 1 to means 2.

Figure 5:
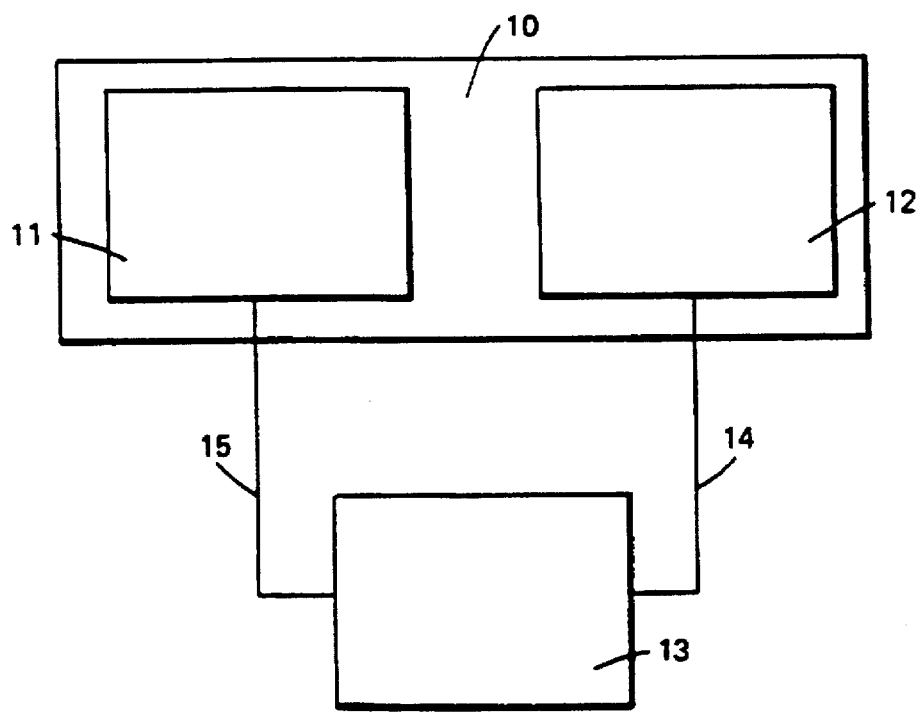
FIG. 5 shows a diagrammatic representation of another apparatus in accordance with the present invention.

Referring now to FIG. 5 of the accompanying drawings there is shown a diagrammatic representation of another apparatus in accordance with the present invention said apparatus having a unit 10 which has a reaction unit 11, a detector means 12 (which includes a capillary electrophoresis apparatus) and a means 13 for selecting a sequencing agent to be applied to an oligosaccharide entity; said means 13 includes a logic unit.

In operation an oligosaccharide entity is introduced into the reaction unit 11 and a first selected sequencing agent, or a first selected combination of sequencing agents, is introduced. The reaction products thus obtained are detected by the detector means 12 and the output of the detector means 12 is passed to the means 13 by a link indicated as 14. The output of means 13 is fed back to reaction unit 11, by a link indicated as 15, whereby a second selected sequencing agent, or a second selected combination of sequencing agents, is applied to the oligosaccharide entity, or a product thereof produced by the effect of the first selected sequencing agent, or the first selected combination of sequencing agents, upon the oligosaccharide entity.

By way of example, a third sequencing agent, or a third combination of sequencing agents, may be applied on the basis of results obtained by applying the second sequencing agent, or second combination of sequencing agents, and so on.

Thus, it is possible to achieve a "loop" in which information obtained by applying a sequencing agent, or a combination of sequencing agents, to an oligosaccharide entity, in reaction unit 11, as detected by detector means 12, is fed to means 13 and the selection of sequencing agent, or sequencing agents, to be next applied, as made by means 13, is fed to reaction unit 11 such that an interactive cycle may be established. It will be appreciated that, for example, a cycle of applying a sequencing agent, analysis, and application of a further sequencing agent may be repeated until as many sequencing agents as desired have been used. Thus, for example, apparatus as hereinbefore described with reference to FIG. 5 of the accompanying drawings may be arranged to be fully automated such that a sample oligosaccharide entity may be introduced into reaction unit 11 and the apparatus allowed to function until sequencing of an oligosaccharide structure of an oligosaccharide entity ceases, or a desired degree of sequencing has taken place.

Figure 6:
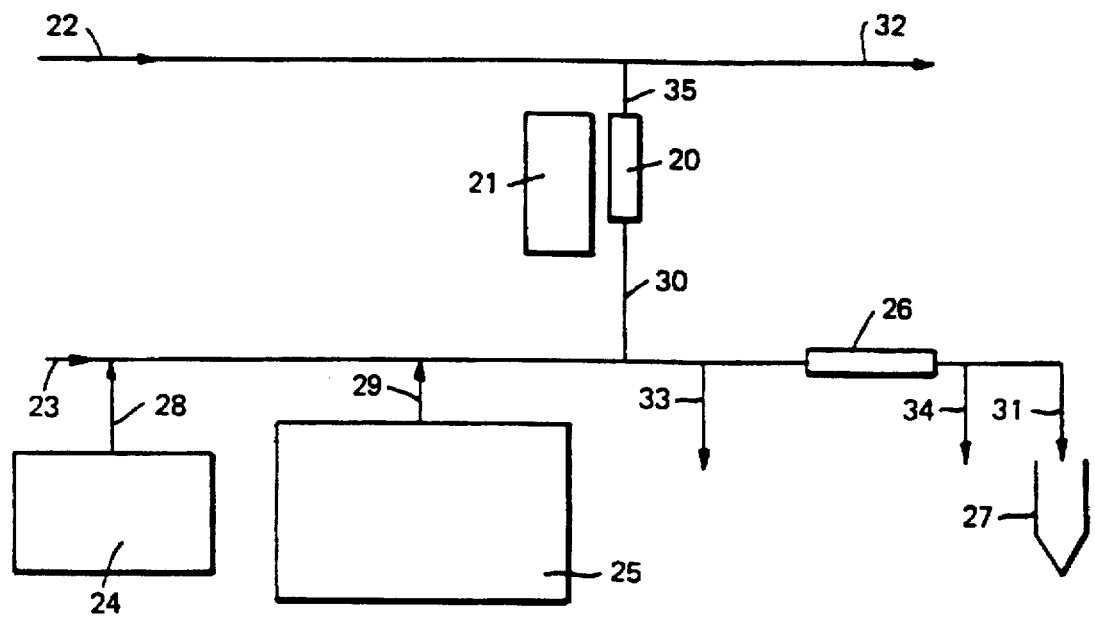
FIG. 6 shows a diagrammatic representation of an apparatus for use in accordance with the present invention.

Referring now to FIG. 6 of the accompanying drawings there is shown a diagrammatic representation of apparatus for use in accordance with the present invention which apparatus has a reaction vessel 20, a heater 21 for heating the reaction vessel 20, a supply line 22, a supply line 23, a buffer reagent storage means 24, a sequencing agent storage means 25 (which may be provided with a cooling means (not shown)), a separation means 26 and a collection vessel 27.

In operation an oligosaccharide entity to be subjected to sequencing may be attached to a support material to form a conjugated material and the conjugated material located in the reaction vessel 20. By application of nitrogen gas through supply lines 22 and 23 and, as appropriate, the use of valves (not shown in this diagrammatic representation), a buffer reagent or reagents may be moved from the buffer reagent storage means 24, (via line 28, and supply line 23 and line 30) to the reaction vessel 20, and a sequencing agent, or agents, may be moved from the sequencing agent storage means 25 (via line 29, a supply line 23 and line 30) to the reaction vessel 20.

Heater 21 may be used to maintain the temperature of the reaction vessel 20 at a selected temperature.

Thus, a sequencing agent, or agents, (together with a buffer reagent, or reagents, as desired) may be applied to the conjugated material in the reaction vessel 20.

By use of nitrogen gas and, as appropriate, the use of valves (not shown in this diagrammatic representation), reaction products formed in the reaction vessel 20 may be removed from the reaction vessel 20 (via line 30 and supply line 23), passed through the separation means 26, which may contain a suitable substance for effecting the removal of unwanted material, and collected as a sample, via line 31, in collection vessel 27.

The sample in collection vessel 27 may be subjected to any suitable analysis (e.g. by use of a capillary electrophoresis apparatus (not shown)) and the results of analysis supplied to a means (not shown) for selecting a sequencing agent to be applied to an oligosaccharide entity such that a further sequencing agent, or further sequencing agents, may be selected and supplied to the reaction vessel 20 from the sequencing agent storage means 25 (together with buffer reagent from the buffer reagent storage means 24 as desired). In this way a "loop" may be established which enables an iterative cycle to be effected in which sequencing may be carried out.

If desired, the line 31 may be arranged to supply a sample directly to an analysing means (not shown) (e.g. a means which includes a capillary electrophoresis apparatus) rather than to collection vessel 27.

Waste lines 32, 33 and 34 may be provided, as necessary, for the discharge of unwanted materials from the apparatus.

Line 35 is provided so as to permit reaction vessel 20 to be connected (via valves (not shown) as appropriate) with supply line 22 or waste line 32 as may be desired.

Figure 7:
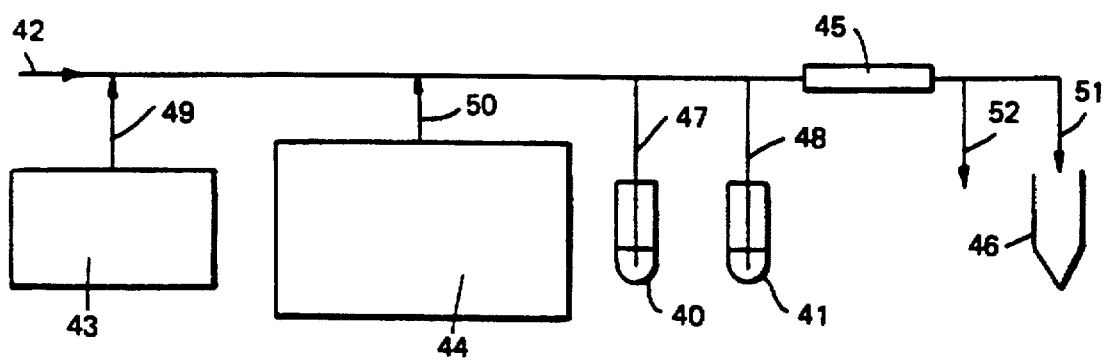
FIG. 7 shows a diagrammatic representation of further apparatus for use in accordance with the present invention.

Referring now to FIG. 7 of the accompanying drawings there is shown a diagrammatic representation of further apparatus for use in accordance with the present invention which apparatus has an oligosaccharide entity storage vessel 40, a reaction vessel 41 (which may be provided, for example, with a heater (not shown)), a supply line 42, a buffer reagent storage means 43, a sequencing agent storage means 44 (which may be provided with a cooling means (not shown)), a separation means 45 and a collection vessel 46.

In operation a supply of solution containing an oligosaccharide entity to be subjected to sequencing in accordance with the present invention is placed in the oligosaccharide entity storage vessel 40. Subsequently, by the application of nitrogen gas through supply line 42 and, as appropriate, the use of valves (not shown in this diagrammatic representation) a sample of the oligosaccharide entity may be moved (via line 47 and supply line 42 and line 48) from the oligosaccharide storage vessel 40 to the reaction vessel 41 and, also, buffer reagent, or reagents, may be moved from the buffer reagent storage means 43 (via line 49, supply line 42 and line 48) to the reaction vessel 41, and, further, a sequencing reagent, or reagents, may be moved from the sequencing reagent storage means 44 (via line 50, supply line 42 and line 48) to the reaction vessel 41.

Thus, a sequencing agent, or agents, (together with a buffer reagent, or reagents, as desired) may be mixed with a sample of oligosaccharide entity taken from the supply of oligosaccharide entity.

By use of nitrogen gas and, as appropriate, the use of valves (not shown in this diagrammatic representation), reaction products formed in the reaction vessel 41 may be moved (via line 48 and supply line 42), passed through the separation means 45, which may contain a suitable substance for effecting the removal of unwanted material, and collected as a sample, via line 51, in collection vessel 46.

The sample in collection vessel 46 may be subjected to any suitable analysis (e.g. by use of a capillary electrophoresis apparatus (not shown) and the results of analysis supplied to a means (not shown) for selecting a sequencing agent to be applied to an oligosaccharide entity such that a further sequencing agent, or further sequencing agents, may be selected and supplied (from the sequencing agent storage means 44) to a fresh sample of oligosaccharide entity (from the oligosaccharide entity storage vessel 40) in reaction vessel 41 (together with buffer reagent from the buffer reagent storage means 43 as desired). In this way a "loop" may be established which enables an iterative cycle to be effected in which sequencing may be carried out.

If desired, the line 46 may be arranged to supply a sample directly to an analysing means (not shown) (e.g. a means which includes a capillary electrophoresis apparatus) rather than to collection vessel 46.

Waste line 52 may be provided, as necessary, for the discharge of unwanted materials from the apparatus.

EXAMPLE 1

Figure 28:
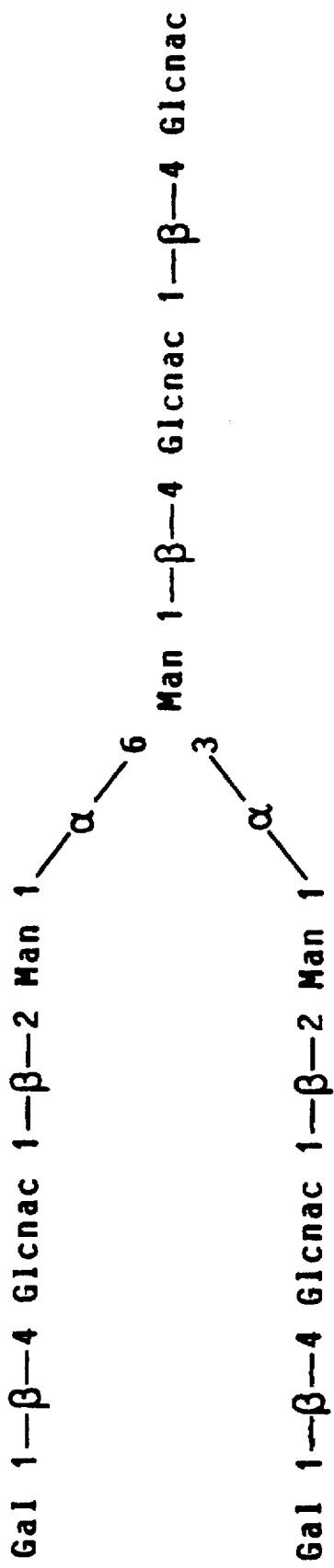
FIG. 28 shows a structure of an oligosaccharide entity to which reference is made in Example 1.
Figure 29:
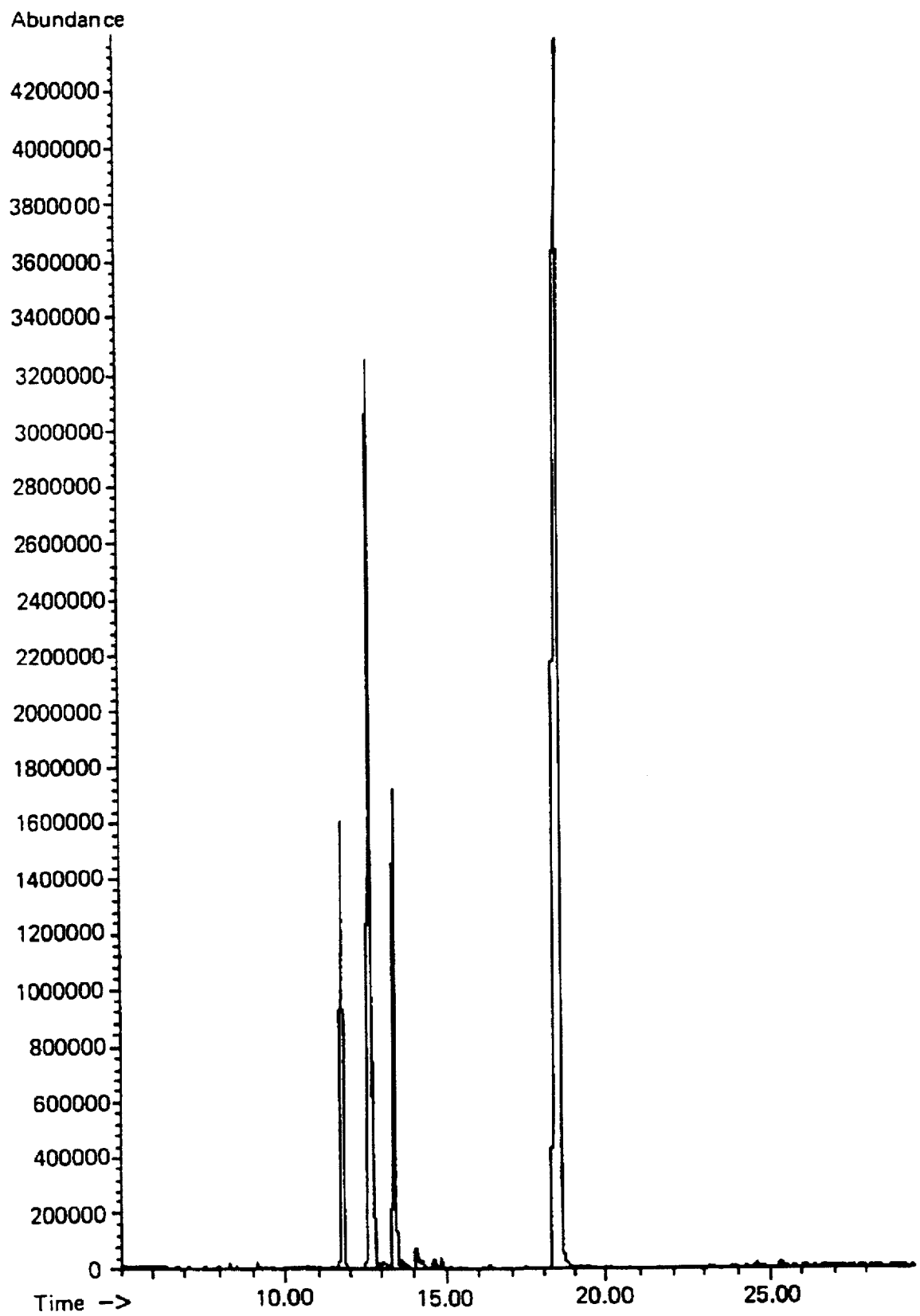
FIG. 29 shows a total ion current chromatogram of TMS-methyl glycosides obtained as disclosed in relation to Example 1(a)
Figure 30:
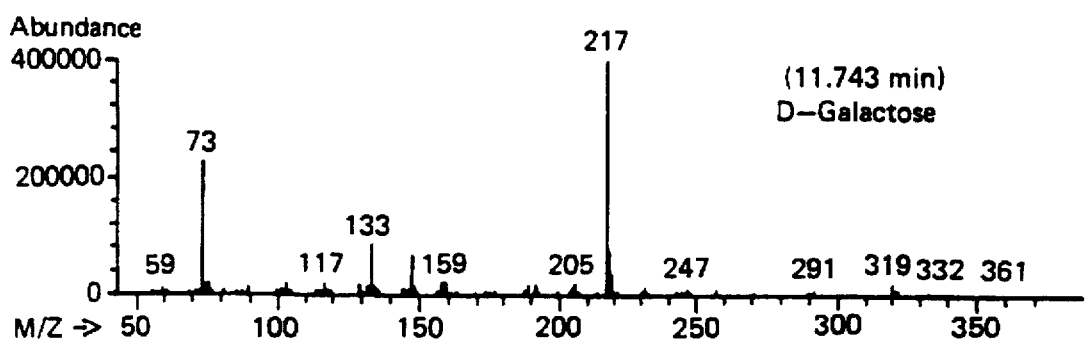
FIGS. 30 to 33 show Gas Chromatography-Mass Spectra for TMS-methyl glycosides obtained as disclosed in relation to Example 1(a)
Figure 31:
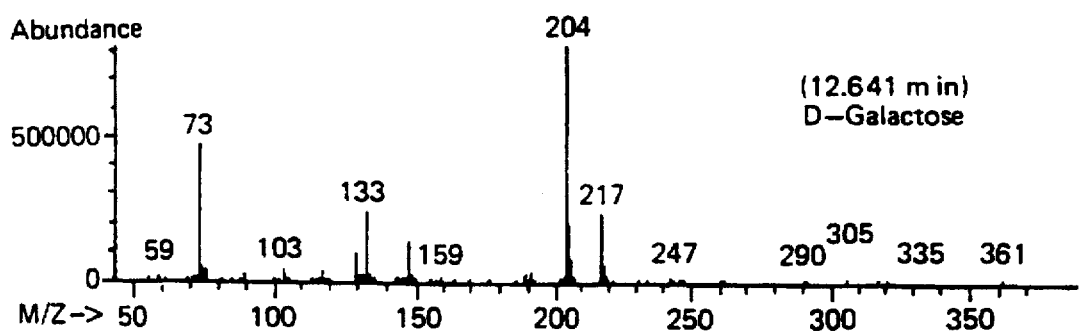
Figure 32:
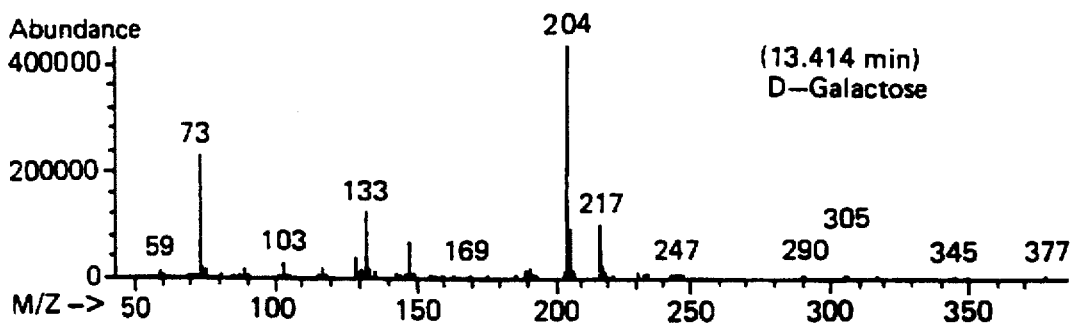
Figure 33:
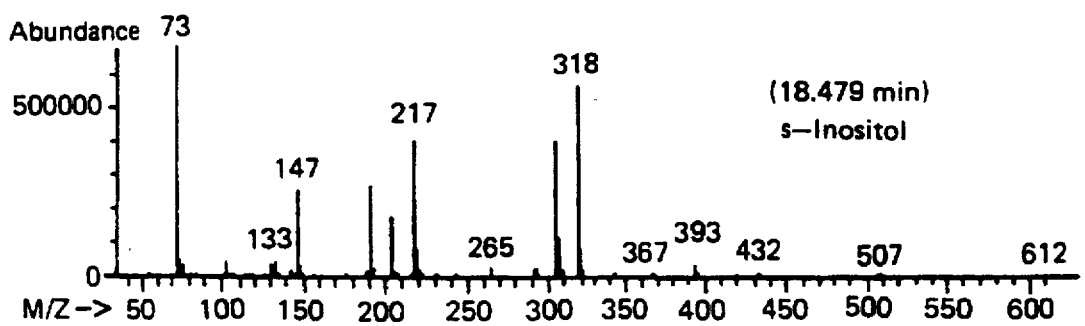
Figure 34:
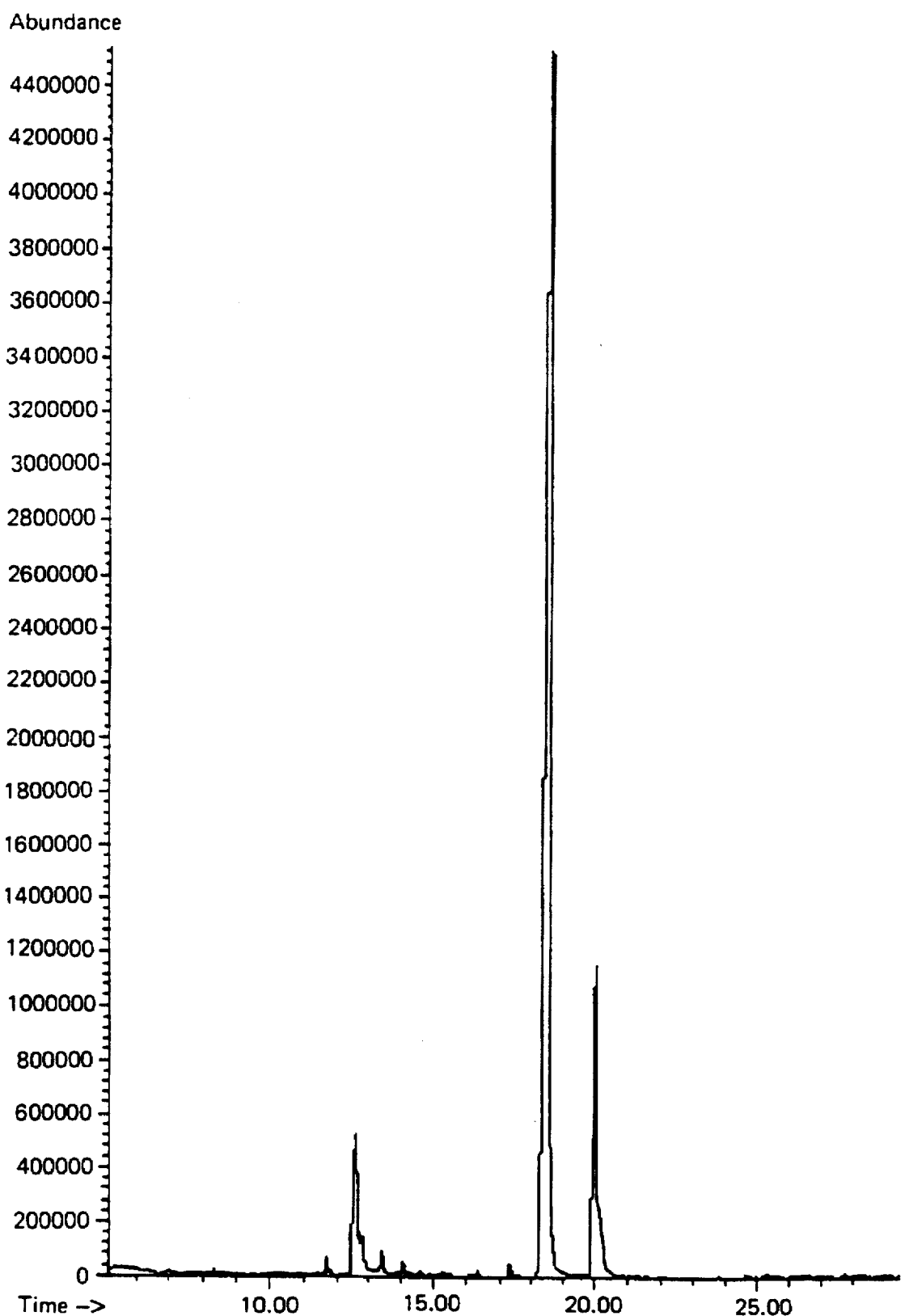
FIG. 34 shows a total ion current chromatogram of TMS-methyl glycosides obtained as disclosed in relation to Example 1(b)
Figure 35:
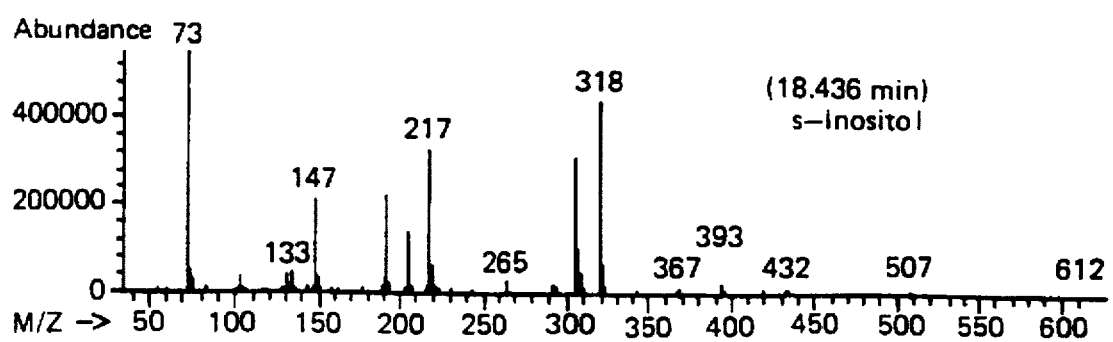
FIGS. 35 to 37 show Gas Chromatography-Mass Spectra for TMS-methyl glycosides obtained as disclosed in relation to Example 1(b)
Figure 36:
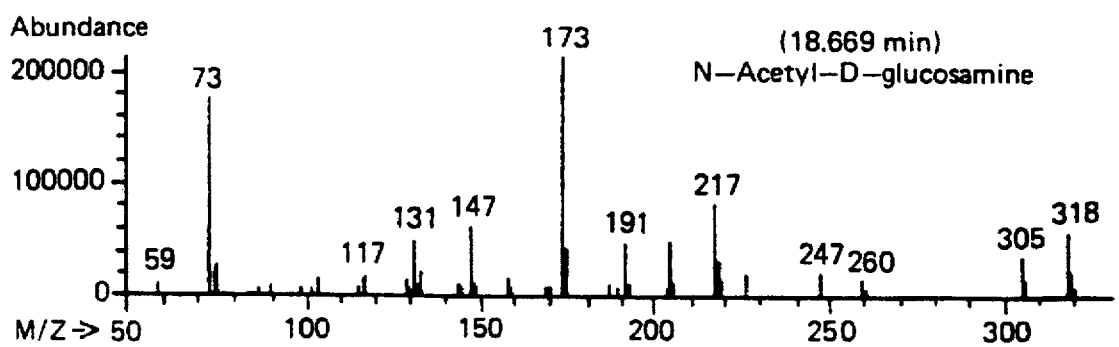
Figure 37:
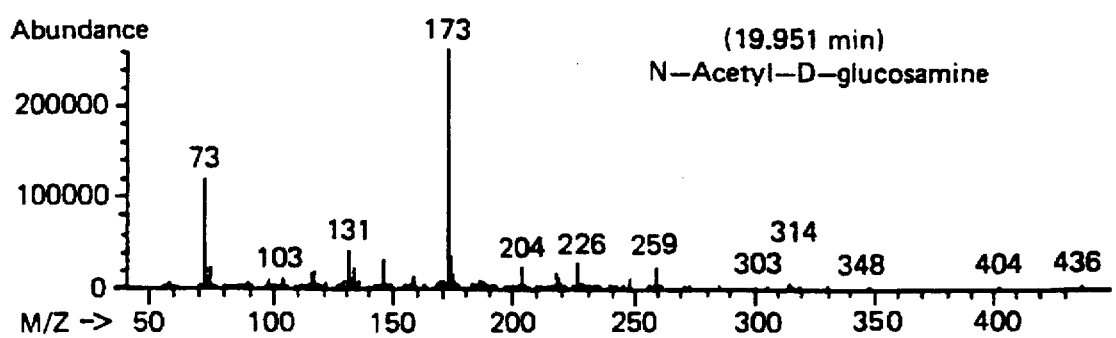
Figure 38:
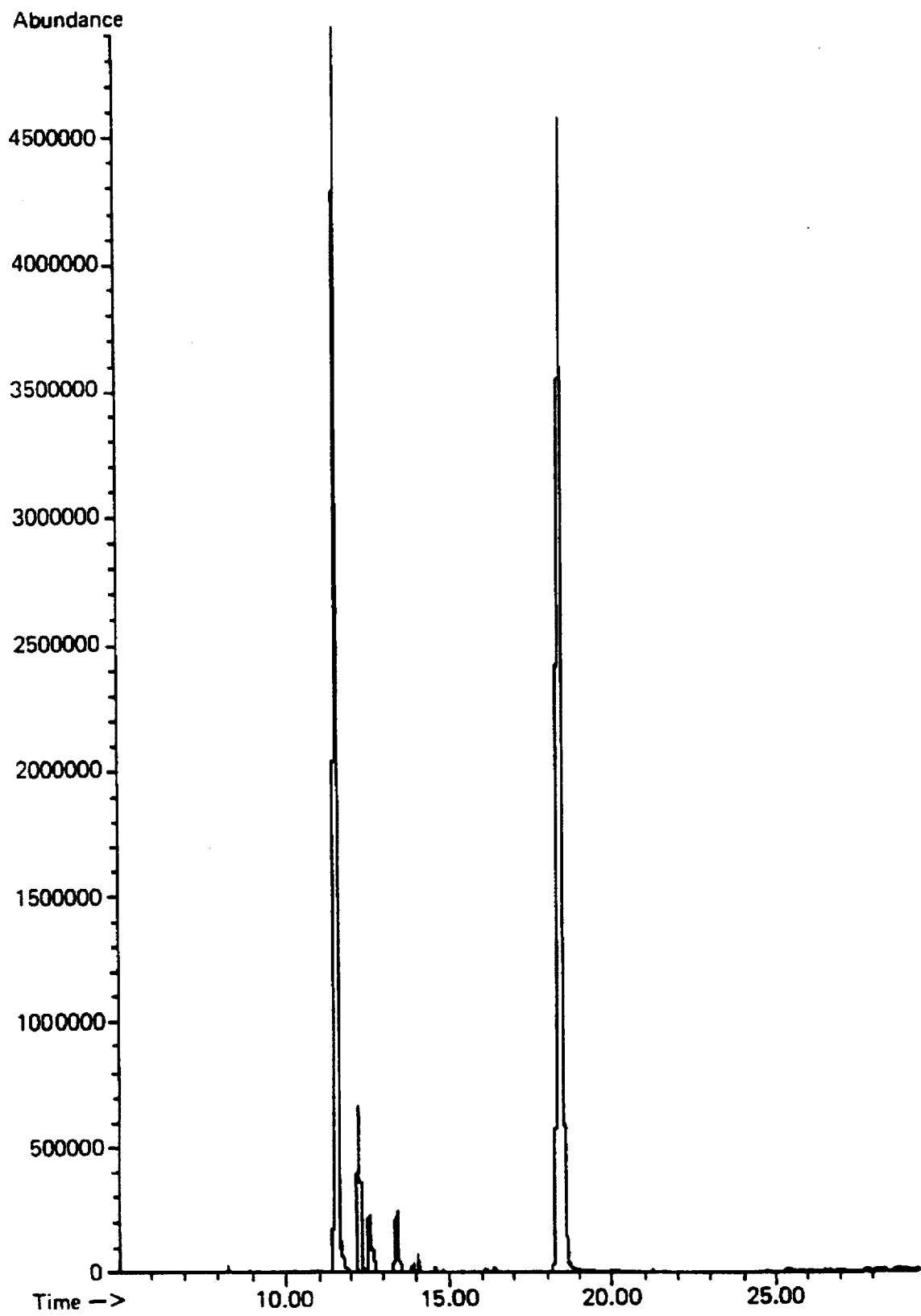
FIG. 38 shows a total ion current chromatogram of TMS-methyl glycosides obtained as disclosed in relation to Example 1(c)
Figure 39:
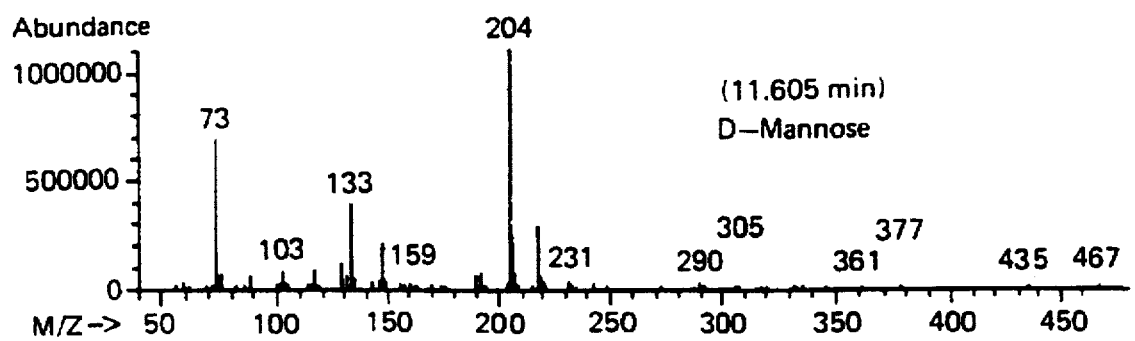
FIGS. 39 to 41 show Gas Chromatography-Mass Spectra of TMS-methyl glycosides obtained as disclosed in relation to Example 1(c)
Figure 40:
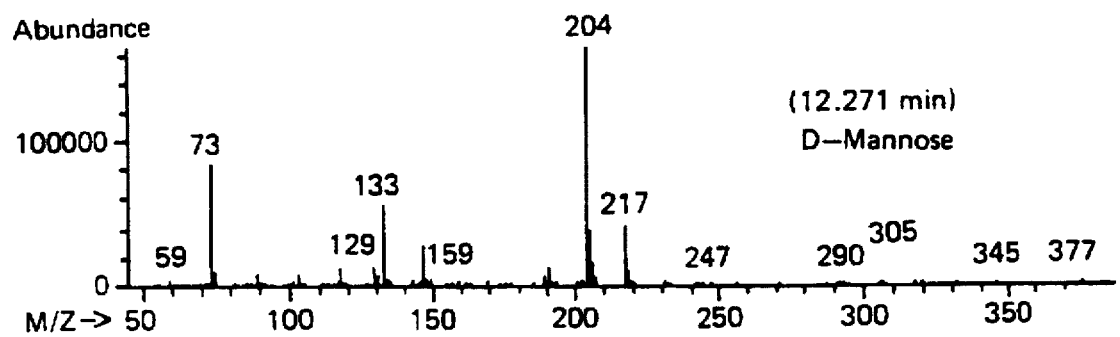
Figure 41:
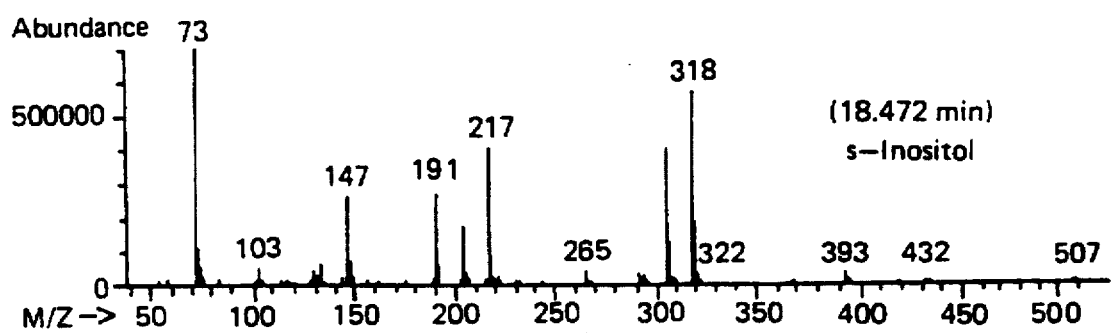

In this Example an oligosaccharide entity comprising an oligosaccharide of the structure given in FIG. 28 of the accompanying drawings was used to demonstrate use of the present invention.

The oligosaccharide was confirmed as having a purity of >95% by 500 MH$_3$ $^1$H-NMR (1-dimensional) and high performance anion-exchange chromatography.

The oligosaccharide was immmobilised by being conjugated to a support material comprising. 1,1' carbonyl diimidazole-activated agarose using reductive amination as follows:

1 mg of the oligosaccharide was heated with 80 µl of a reagent prepared by dissolving 100 mg 2-amino pyridine in 65 µl of concentrated hydrochloric acid at 90° C. for 12 minutes. Subsequently, 8 µl of a dimethyl sulphoxide solution of sodium cyanoborohydride at concentration 1.66 gm/ml was added and the resulting mixture heated at 90° C. for a further 90 minutes. After cooling, the mixture was diluted with 0.5 ml n-butanol:ethanol (4:1) then applied to a column of cellulose (4 ml) and eluted with 20 ml n-butanol:ethanol:water [4:4:1], followed by methanol (3 ml) then water (5 ml). The methanol and water fractions were combined and concentrated by rotary-evaporation to 0.2 ml. A slurry of diimidazolecarbonyl activated agarose in acetone (0.5 ml) was added and the resulting mixture stirred at room temperature for 24 hours.

The combination of oligosaccharide conjugated to the support material (which combination will be referred to as "conjugated material" in this Example) was separated from reaction mixture and any unconjugated substances by rinsing in 0.1M sodium chloride followed by centrifugation (1000 g for 1 minute), the liquid supernatant being discarded; the rinsing, centrifugation and discarding of liquid was repeated five times.

The immobilised oligosaccharide was subjected to sequencing by incubating conjugated material with exoglycosidases and identifying and quantifying any released monosaccharides as follows:

A preliminary analysis of the oligosaccharide was carried out and the following monosaccharide units were identified: Man (3 units), Gal (2 units) and Glcnac (4 units).

Figure 8:
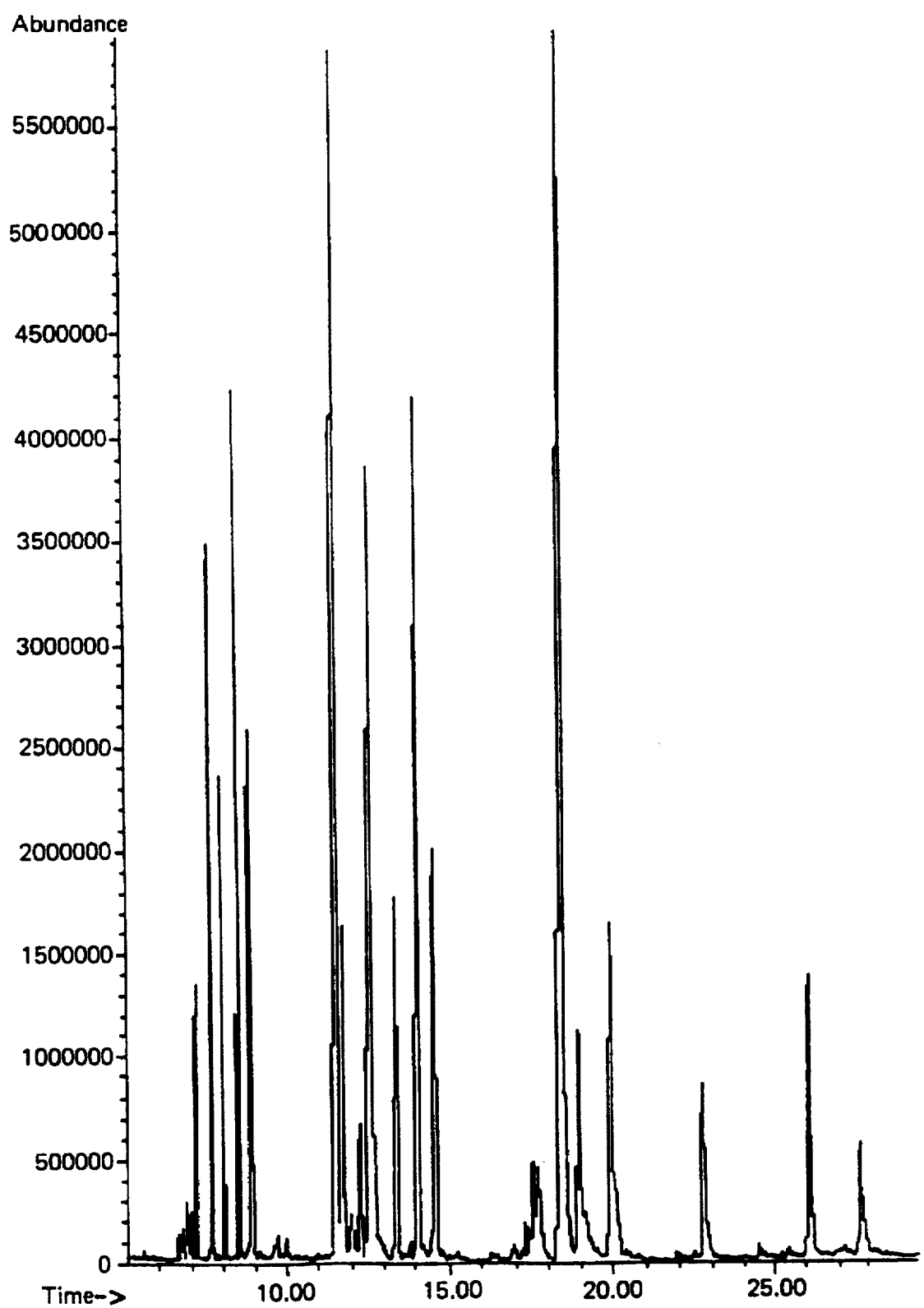
FIG. 8 shows a total ion current chromatogram of TMS-methyl glycosides of standard monosaccharides.
Figure 9:
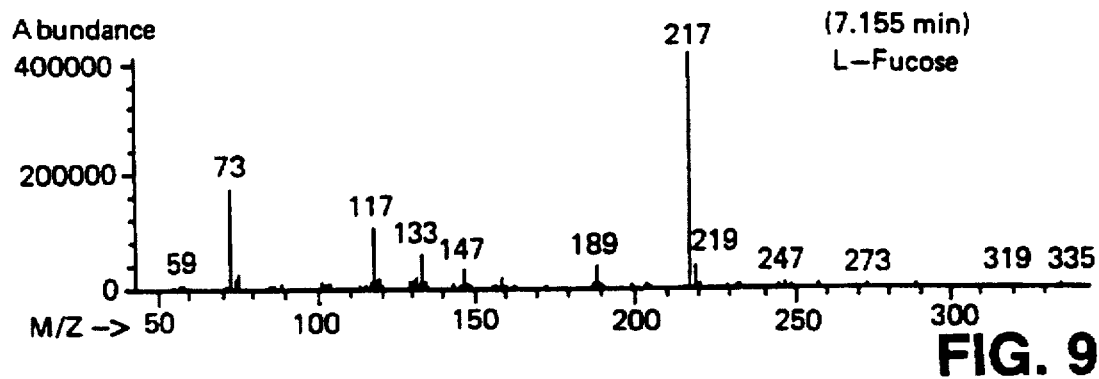
FIGS. 9 to 27 show Gas Chromatography-Mass Spectra for TMS-methyl glycosides of standard monosaccharides. The relevant monosaccharide is indicated in the top right-hand corner of each Figure; it will be appreciated that M/Z in the Figures indicates mass/charge ratio.
Figure 10:
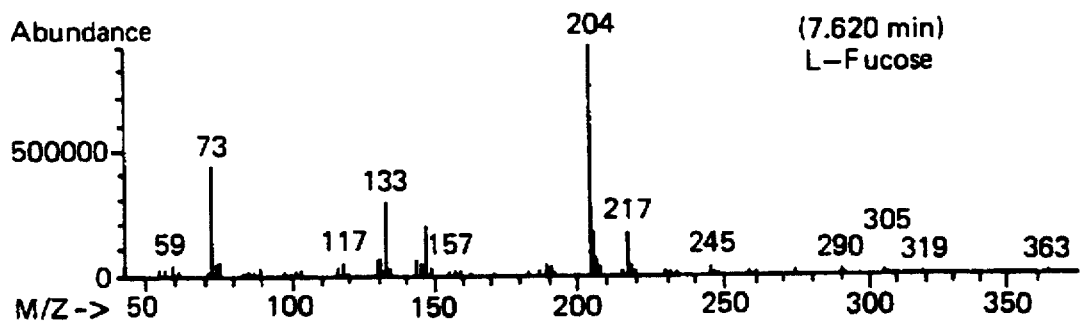
Figure 11:
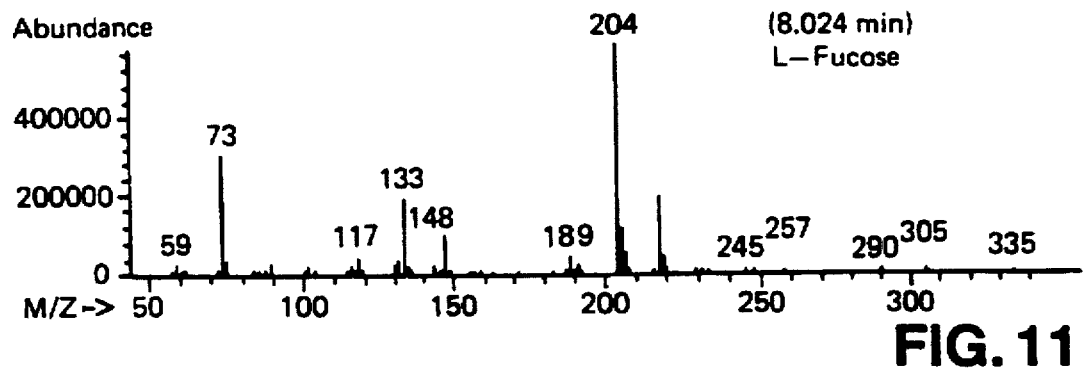
Figure 12:
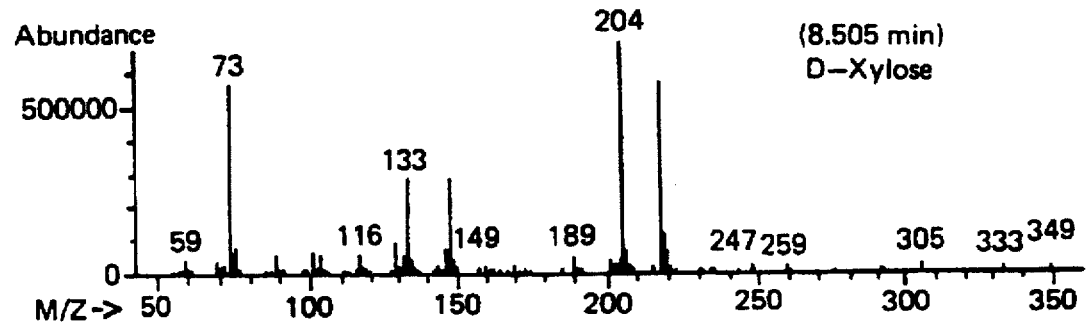
Figure 13:
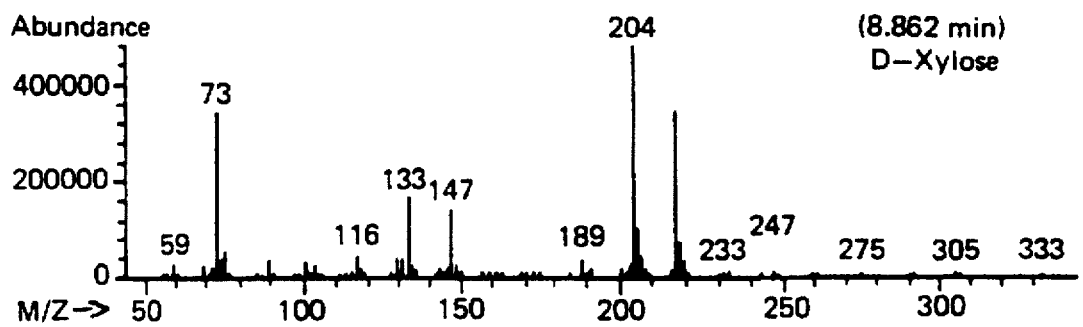
Figure 14:
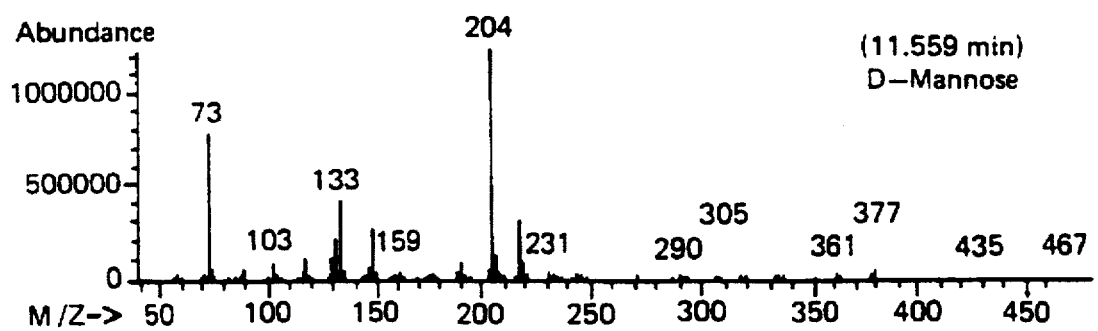
Figure 15:
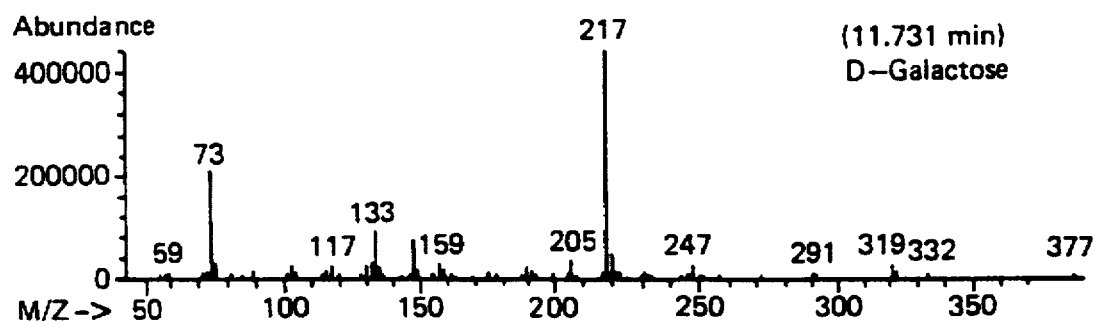
Figure 16:
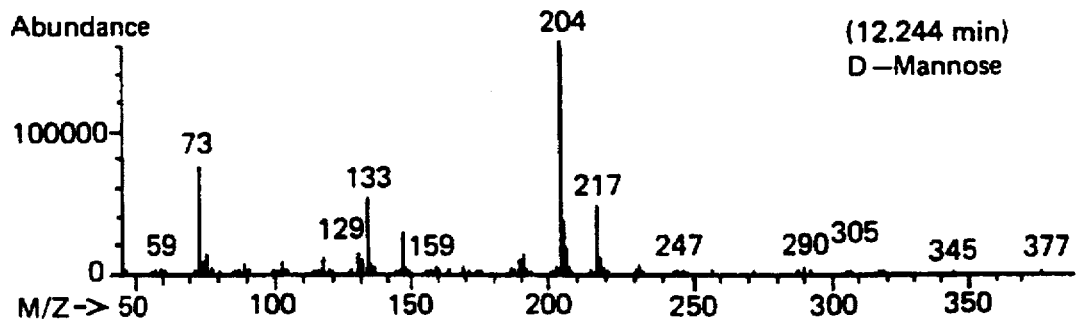
Figure 17:
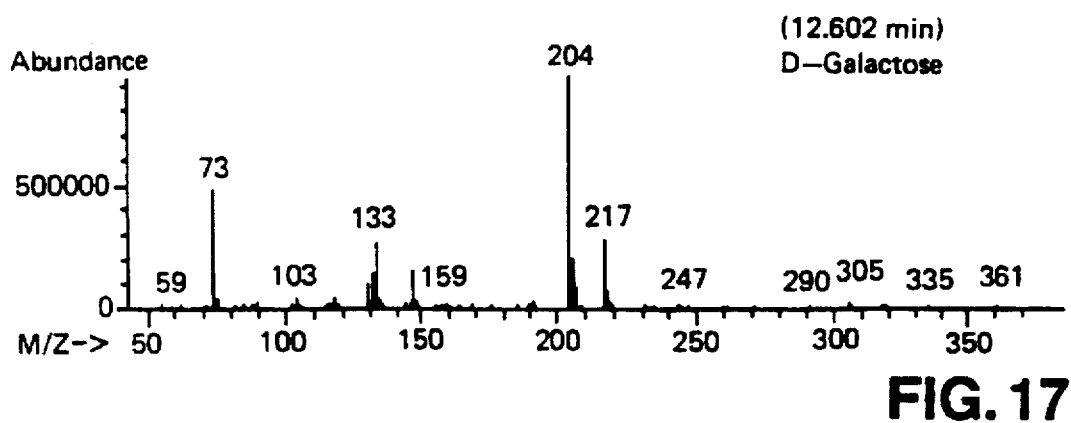
Figure 18:
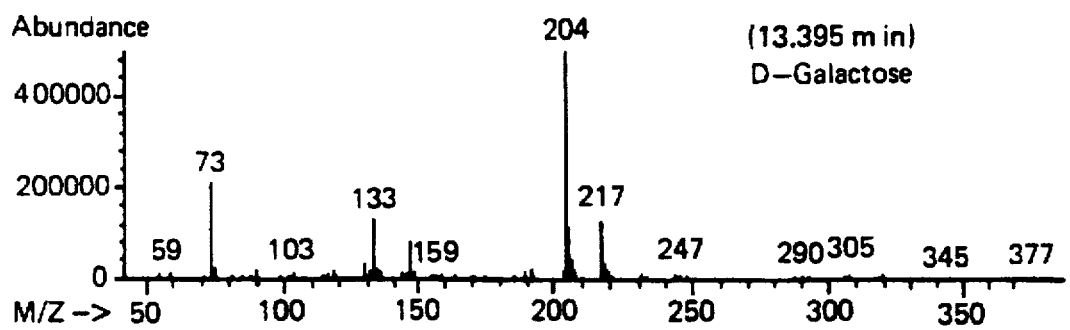
Figure 19:
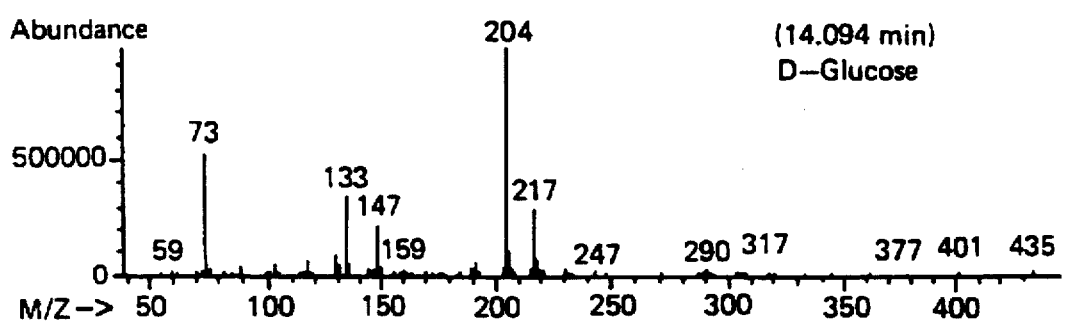
Figure 20:
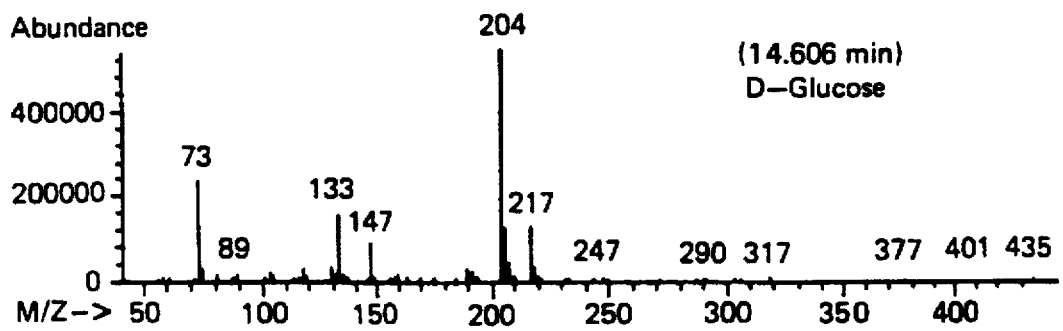
Figure 21:
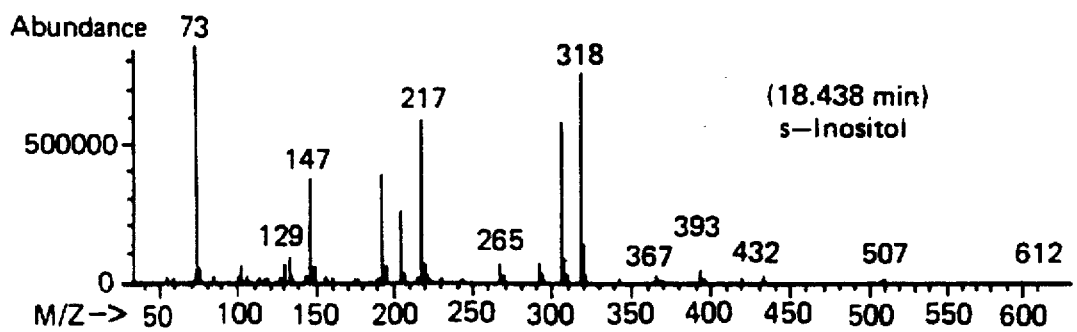
Figure 22:
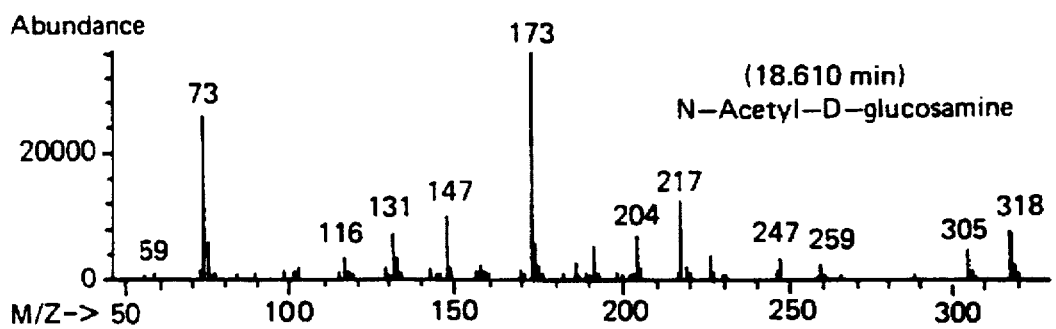
Figure 23:
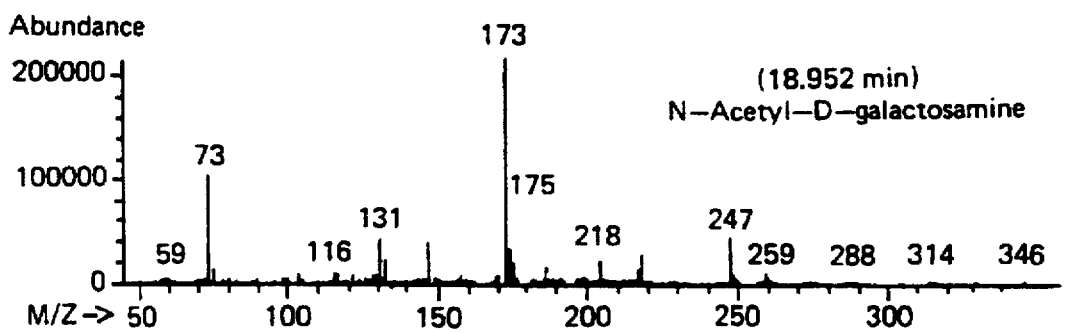
Figure 24:
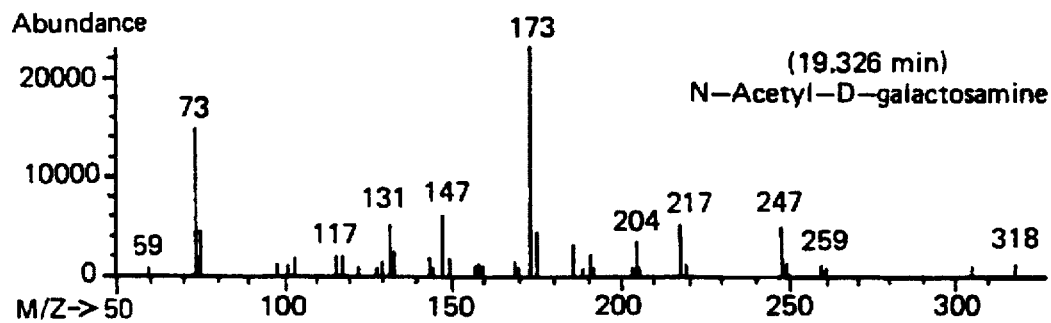
Figure 25:
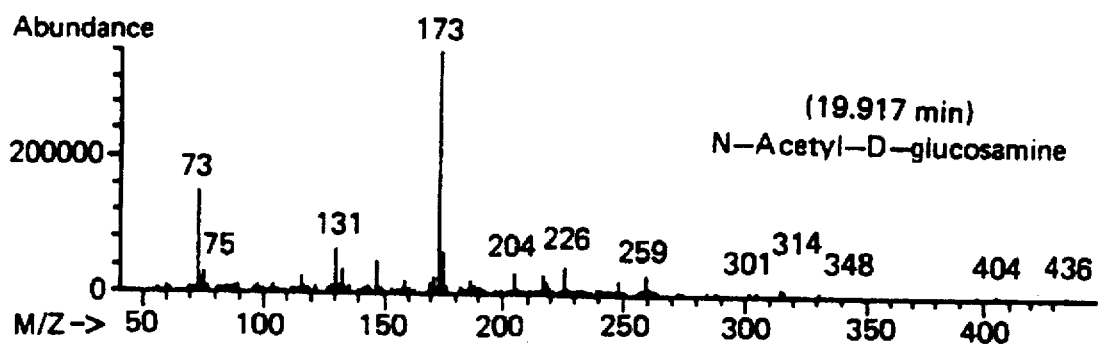
Figure 26:
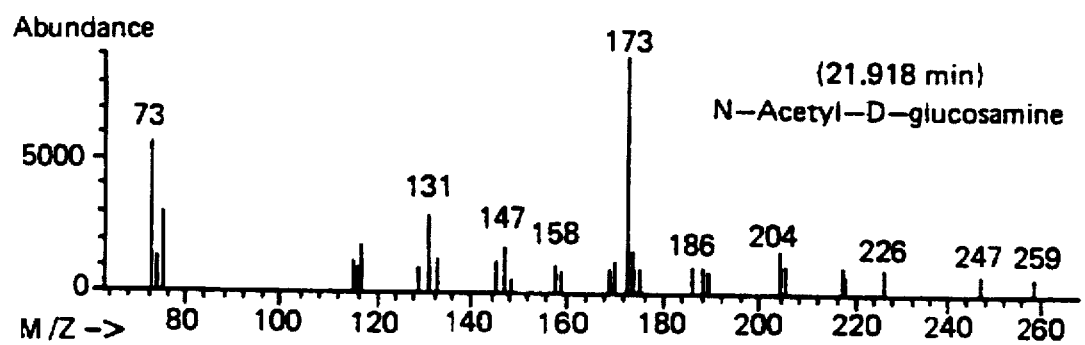
Figure 27:
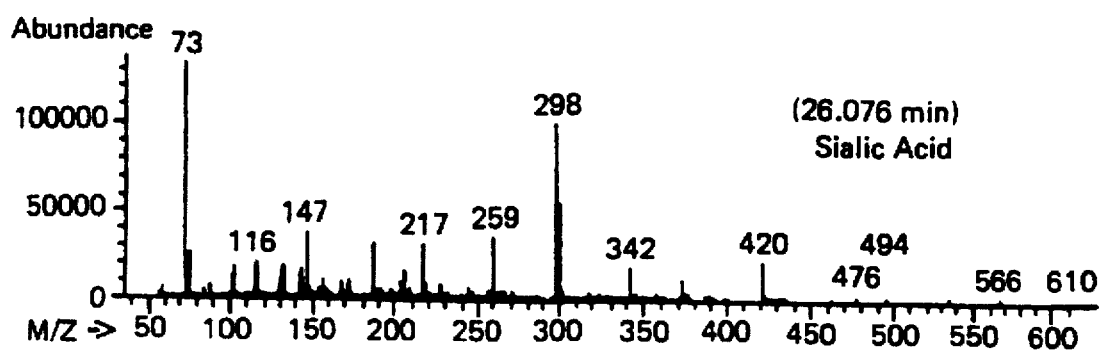

The results of the preliminary analysis were used, in conjunction with a means for selecting a sequencing agent to be applied to an oligosaccharide entity (said means including a logic unit), to identify candidate structures and to select a sequencing agent to be applied to the conjugated material. Thus:

(a) to conjugated material in a plastic tube was added 100 µl of a solution consisting of 0.1M sodium citrate/phosphate, pH 3.5 containing 1.0 unit of purified β-D-galactosidase enzyme (obtained from jack bean) to form a mixture. The tube was capped and the mixture incubated at 37° C. for 6 hours. Conjugated material was separated by rinsing in 0.1M sodium chloride followed by centrifugation (1000 g for 1 minute). Liquid supernatant was separated from conjugated material and collected. This was repeated and all liquid supernatant was pooled and desalted by passage through an ion-exchange column consisting of 0.5 ml Dowex AG50X 12(H$^+$) resin below 0.5 ml Dowex AG3X 4A(OH$^-$) resin. (Both resins were purchased from Bio RAD.) Eluent from the column was collected, rotary-evaporated to dryness and converted to the 1-O-methyl trimethylsilyl glycoside exactly according to the standard procedure of Chaplin (Analytical Biochemistry 123 p.336 (1982)). The resulting 1-O-methyl trimethylsilyl glycoside was quantitated by GC-MS and identified by reference to known standard compounds based on retention time during GC and mass spectrum. The total ion current chromatogram of standard monosaccharides is shown in FIG. 8 of the accompanying drawings and mass spectra of standard monosaccharides are shown in FIGS. 9 to 27 of the accompanying drawings. The total ion current chromatogram and mass spectra for the liquid supernatant recovered after incubating the conjugated material with the β-D-galactosidase are shown respectively in FIGS. 29 and 30 to 33 of the accompanying drawings. From this information it can be concluded that the action of the β-D-galactosidase led to the separation from the conjugated material of 511 nanomoles of galactose and of no other monosaccharide;

(b) the information obtained in (a) above was used in conjunction with a means for selecting a sequencing agent to be applied to an oligosaccharide entity (said means including a logic unit), to select a further sequencing agent to be applied to the conjugated material obtained after treatment as disclosed in (a) above.

Thus to conjugated material (as obtained after treatment as disclosed in (a) above) in a plastic tube was added 100 µl of a solution consisting of 0.1M sodium cacodylate, pH 6.0 containing 48 microunits of purified β-N-acetyl-D-hexosaminidase enzyme (obtained from Streptococcus pneumoniae) to form a mixture. The tube was capped and the mixture incubated at 37° C. for 6 hours. Conjugated material was separated by rinsing in 0.1M sodium chloride followed by centrifugation (1000 g for 1 minute). Liquid supernatant was separated from conjugated material and collected. This was repeated and all liquid supernatant was pooled and desalted by passage through an ion-exchange column consisting of 0.5 ml Dowex AG50X 12(H$^+$) resin below 0.5 ml Dowex AG3X 4A(OH$^-$) resin. (Both resins were purchased from Bio RAD.) Eluent from the column was collected, rotary-evaporated to dryness and converted to the 1-O-methyl trimethylsilyl glycoside exactly according to the standard procedure of Chaplin (Analytical Biochemistry 123 p.336(1982)). The resulting 1-O-methyl trimethylsilyl glycoside was quantitated by GC-MS and identified by reference to known standard compounds based on retention time during GC and mass spectrum. The total ion current chromatogram of standard monosaccharides is shown in FIG. 8 of the accompanying drawings and mass spectra of standard monosaccharides are shown in FIGS. 9 to 27 of the accompanying drawings. The total ion current chromatogram and mass spectra for the liquid supernatant recovered after incubating the conjugated material with the β-N-acetyl-D-hexosaminidase are shown respectively in FIG. 34 and FIGS. 35 to 37 of the accompanying drawings. From this information it can be concluded that the action of the β-N-acetyl-D-hexosaminidase led to the separation from the conjugated material of 487 nanomoles of N-acetylglucosamine and of no other monosaccharide;

(c) the information obtained in (b) above was used in conjunction with a means for selecting a sequencing agent to be applied to an oligosaccharide entity (said means including a logic unit), to select a further sequencing agent to be applied to the conjugated material obtained after treatment as disclosed in (b) above.

Thus, to conjugated material (as obtained after treatment as disclosed in (b) above) in a plastic tube was added 100 µl of a solution consisting of 0.1M sodium acetate/0.01M zinc acetate, pH 5.0 containing 6 units of the purified α-D-mannosidase enzyme (obtained from jack bean) to form a mixture. The tube was capped and the mixture incubated at 37° C. for 6 hours. Conjugated material was separated by rinsing in 0.1M sodium chloride followed by centrifugation (1000 g for 1 minute). The liquid supernatant was separated from conjugated material and collected. This was repeated and all liquid supernatant was pooled and desalted by passage through an ion-exchange column consisting of 0.5 ml Dowex AG50X 12(H$^+$) resin below 0.5 ml Dowex AG3X 4A(OH$^-$) resin. (Both resins were purchased from Bio RAD.) Eluent from the column was collected, rotary-evaporated to dryness and converted to the 1-O-methyl trimethylsilyl glycoside exactly according to the standard procedure of Chaplin (Analytical Biochemistry 123 p.336 (1982)). The resulting 1-O-methyl trimethylsilyl glycoside was quantitated by GC-MS and identified by reference to known standard compounds based on retention time during GC and mass spectrum. The total ion current chromatogram of standard monosaccharides is shown in FIG. 8 of the accompanying drawings and mass spectra of standard monosaccharides are shown in FIGS. 9 to 27 of the accompanying drawings. The total ion current chromatogram and mass spectra for the liquid supernatant recovered after incubating the conjugated material with the α-D-mannosidase are shown respectively in FIG. 38 and FIGS. 39 to 41 of the accompanying drawings. From this information it can be concluded that the action of the α-D-mannosidase led to the separation from the conjugated material of 527 nanomoles of mannose and of no other monosaccharide;

(d) the information obtained in (c) above was used, in conjunction with a means for selecting a sequencing agent to be applied to an oligosaccharide entity (said means including a logic unit), to select a further sequencing agent to be applied to the conjugated material obtained after treatment as disclosed in (c) above.

Thus, to conjugated material (as obtained after treatment as disclosed in (c) above) in a plastic tube was added 100 µl of a solution consisting of 0.1M sodium acetate, pH 4.0 containing 0.3 units of the purified β-D-mannosidase enzyme (obtained from Helix pomatia) to form a mixture. The tube was capped and the mixture incubated at 37° C. for 6 hours. Conjugated material was separated by rinsing in 0.1M sodium chloride followed by centrifugation (1000 g for 1 minute). The liquid supernatant was separated from conjugated material and collected. This was repeated and all liquid supernatant was pooled and desalted by passage through an ion-exchange column consisting of 0.5 ml Dowex AG50X 12(H$^+$) resin below 0.5 ml Dowex AG3X 4A(OH$^-$) resin. (Both resins were purchased from Bio RAD.) Eluent from the column was collected, rotary-evaporated to dryness and converted to the 1-O-methyl trimethylsilyl glycoside exactly according to the standard procedures of Chaplin (Analytical Biochemistry 123 p.336 (1982)). The resulting 1-O-methyl trimethylsilyl glycoside was quantitated by GC-MS and identified by reference to known standard compounds based on retention time during GC and mass spectrum. The total ion current chromatogram of standard monosaccharides is shown in FIG. 8 of the accompanying drawings and mass spectra of standard monosaccharide are shown in FIGS. 9 to 27 of the accompanying drawings. The total ion current chromatogram and mass spectra for the liquid supernatant recovered after incubating the conjugated material with the β-D-mannosidase were essentially the same as those shown, respectively, in FIGS. 38 and FIGS. 39 to 41 of the accompanying drawings. From this information it can be concluded that the action of the β-D-mannosidase led to the separation from the conjugated material of 271 nanomoles of mannose and of no other monosaccharide;

(e) the information obtained in (d) above was used, in conjunction with a means for selecting a sequencing agent to be applied to an oligosaccharide entity (said means including a logic unit) to select a further sequencing agent to be applied to the conjugated materials obtained after treatment as disclosed in (d) above.

Thus, to conjugated material (as obtained after treatment as disclosed in (d) above) in a plastic tube was added 100 µl of a solution consisting of 0.1M sodium citrate/phosphate, pH 4.5 containing 2.5 units of the purified β-N-acetyl-D-hexosaminidase (obtained from jack bean) to form a mixture. The tube was capped and the mixture incubated at 37° C. for 6 hours. Conjugated material was separated by rinsing in 0.1M sodium chloride followed by centrifugation (1000 g for 1 minute). The liquid supernatant was separated from conjugated material and collected. This was repeated and all liquid supernatant was pooled and desalted by passage through an ion-exchange column consisting of 0.5 ml Dowex AG50X 12(H$^+$) resin below 0.5 ml Dowex AG3X 4A(OH$^-$) resin. (Both resins were purchased from Bio RAD.) Eluent from the column was collected, rotary-evaporated to dryness and converted to the 1-O-methyl trimethylsilyl glycoside exactly according to the standard procedure of Chaplin (Analytical Biochemistry 123 p.336 (1982)). The resulting 1-O-methyl trimethylsilyl glycoside was quantitated by GC-MS and identified by reference to known standard compounds based on retention time during GC and mass spectrum. The total ion current chromatogram of standard monosaccharides is shown in FIG. 8 of the accompanying drawings and mass spectra of standard monosaccharides are shown in FIGS. 9 to 27 of the accompanying drawings. The total ion current chromatogram and mass spectra for the liquid supernatant recovered after incubating the conjugated material with β-N-acetyl-D-hexosaminidase were essentially the same as those shown, respectively, in FIG. 34 and FIGS. 35 to 37 of the accompanying drawings. From this information it can be concluded that the action of the β-N-acetyl-D-hexosaminidase led to the separation from the conjugated material of 267 nanomoles of N-acetylglucosamine and of no other monosaccharide.

From the information obtained as above disclosed in this Example and the well known specificities of the exoglycosidases employed, it is clear that monosaccharides were released from the conjugated material in the order and ratio stated below:

D-galactose β1→4: 2 residues
N-acetyl-D-glucosamine β1→2: 2 residues
Mannose α1→6,3: 2 residues
Mannose β1→4: 1 residue
N-acetyl-D-glucosamine β1→4: 1 residue The monosaccharide attaching the starting oligosaccharide to the resin is not susceptible to an exoglycosidase enzyme, since it is not attached by an O-glycosidic linkage. This terminal N-acetyl glucosamine (Glcnac) is therefore understood to exist. From this information, the sequence of the initial oligosaccharide can clearly only be that as shown in FIG. 28 of the accompanying drawings.

This sequence is consistent with NMR studies of a solution form of the oligosaccharide.

EXAMPLE 2

Figure 42:
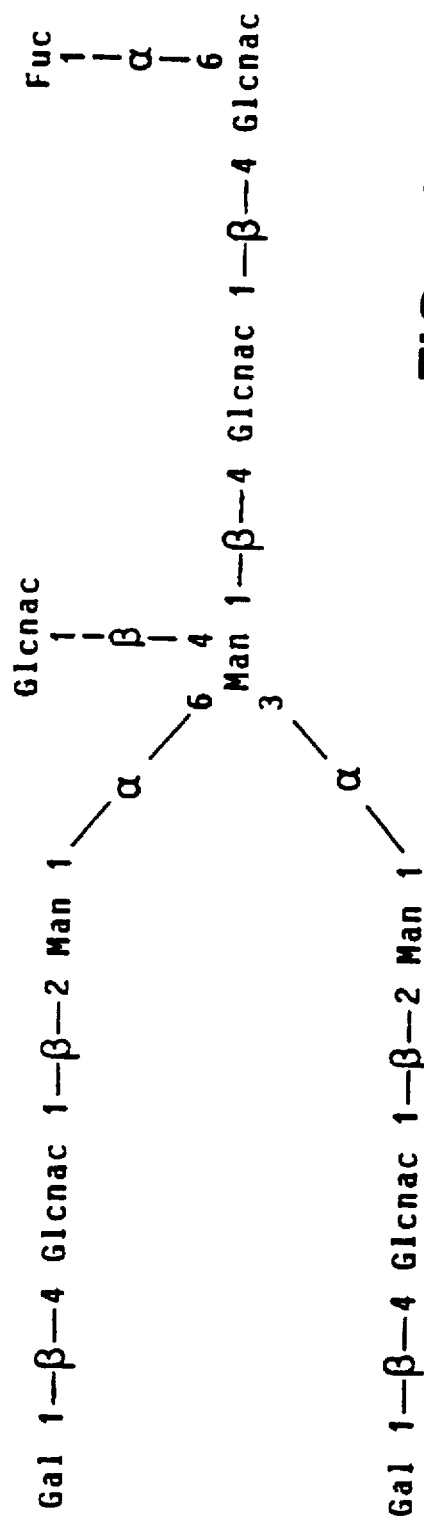
FIG. 42 shows a structure of an oligosaccharide entity to which reference is made in Example 2.

In this Example an oligosaccharide entity comprising an oligosaccharide of the structure given in FIG. 42 of the accompanying drawings was used to demonstrate use of the present invention.

A preliminary analysis of the oligosaccharide was carried out and the following monosaccharide units were identified: Gal (2 units), Glcnac (5 units), Man (3 units), Fuc (1 unit).

The oligosaccharide (0.6 mg) was attached to a support material as disclosed in relation to Example 1 to give a conjugated material.

The results of the preliminary analysis were used, in conjunction with a means for selecting a sequencing agent to be applied to an oligosaccharide entity (said means including a logic unit), to identify candidate structures and to select a sequencing agent to be applied to the conjugated material.

The conjugated material was subjected to successive treatments with various sequencing agents (in this Example exoglycosidase enzymes), the choice of each successive sequencing agent being based upon the results of analysis and use of a means for selecting a sequencing agent to be applied to an oligosaccharide entity (said means including a logic unit); the procedures used in this Example were substantially similar to those disclosed in relation to Example 1.

The order in which the various sequencing agents (exoglycosidases in this Example) were applied and the results are set out in Table 2.

TABLE 2

| Order of Use of Exoglycosidase | Exoglycosidase Used | Exoglycosidase Reaction Condition (all in 100 μl reaction volume) | Monosaccharide Detected | Nanomoles of Monosaccharide Detected |
|---|---|---|---|---|
| 1 | β-D-galactosidase (jack bean) | 1 unit in 0.1M sodium citrate/phosphate, pH 3.5 | Galactose | 374 |
| 2 | β-N-acetyl-D-hexosaminidase (*Streptococcus pneumoniae*) | 48 μunits in 0.1M sodium cacodylate, pH 6.0 | N-acetyl glucosamine | 179 |
| 3 | β-N-acetyl-D-hexosaminidase (jack bean) | 2.5 units in 0.1M sodium citrate phosphate, pH 4.5 | N-acetyl glucosamine | 386 |
| 4 | α-D-mannosidase (jack bean) | 6 units in 0.1M sodium acetate, 0.01M zinc acetate, pH 5.0 | mannose | 366 |
| 5 | β-D-mannosidase (*Helix pomatia*) | 0.3 units in 0.1M sodium acetate, pH 4.0 | mannose | 171 |
| 6 | β-N-acetyl-D-hexosaminidase (jack bean) | 2.5 units in 0.1M sodium citrate phosphate, pH 4.5 | N-acetyl glucosamine | 163 |
| 7 | α-L-fucosidase (bovine epididymis) | 20 milliunits in 20 mM sodium citrate/phosphate pH 6.0 | fucose | 174 |

The order and ratio of monosaccharides release was as follows:

D-galactose β1→4: 2 residues
N-acetyl-D-hexosamine β1→2 (Man α1 residue
N-acetyl-D-hexosamine β1→2 (Man α1→6): 1 residue
N-acetyl-D-hexosamine β1→4 (Man β1→4): 1 residue
D-mannose α1→6,3: 2 residues
D-mannose β1→4: 1 residue
L-fucose α1→6: 1 residue
N-acetyl-D-hexosamine β1→4: 1 residue From this information the sequence of the initial oligosaccharide can clearly only be that as shown in FIG. 42 of the accompanying drawings.

EXAMPLE 3

Figure 43:
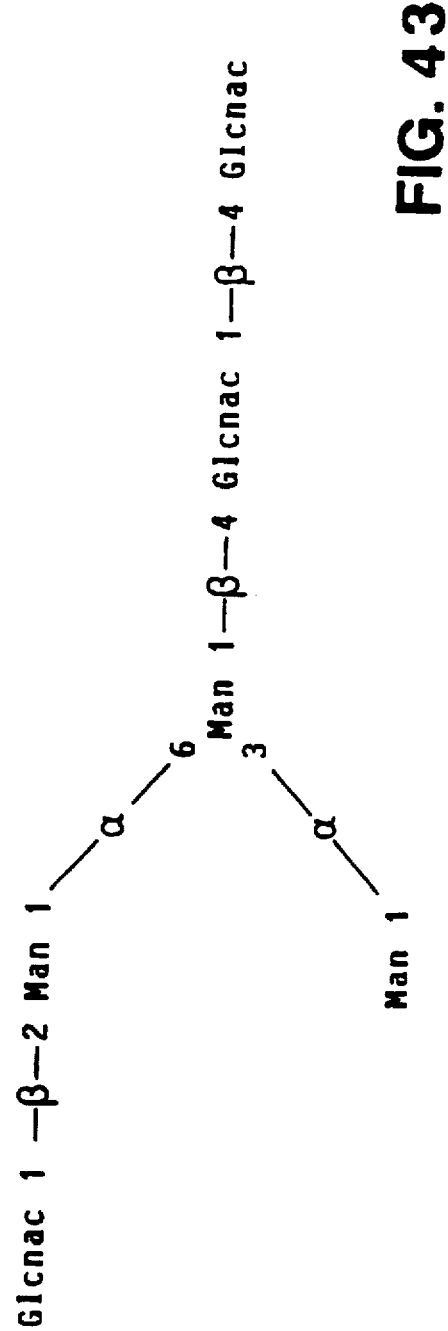
FIG. 43 shows a structure of an oligosaccharide entity to which reference is made in Example 3.

In this Example an oligosaccharide entity comprising an oligosaccharide of the structure given in FIG. 43 of the accompanying drawings was used to demonstrate use of the present invention.

A preliminary analysis of the oligosaccharide was carried out and the following monosaccharide units were identified: Man (3 units), Glcnac (3 units).

The oligosaccharide (0.3 mg) was attached to a support material as disclosed in relation to Example 1 to give a conjugated material.

The results of the preliminary analysis were used, in conjunction with a means for selecting a sequencing agent to be applied to an oligosaccharide entity (said means including a logic unit), to identify candidate structures and to select a sequencing agent to be applied to the conjugated material.

The conjugated material was subjected to successive treatments with various sequencing agents (in this Example exoglycosidase enzymes), the choice of each successive sequencing agent being based upon the results of analysis and use of a means for selecting a sequencing agent to be applied to an oligosaccharide entity (said means including a logic unit); the procedures used in this Example were substantially similar to those disclosed in relation to Example 1.

The order in which the various sequencing agents (exoglycosidases in this Example) were applied and the results are set out in Table 3.

The order and ratio of monosaccharides release was as follows:

D-mannose α1→3: 1 residue
N-acetyl-D-glucosamine β1→2: 1 residue
D-mannose α1→6: 1 residue
D-mannose β1→4: 1 residue
N-acetyl-D-glucosamine β1→4: 1 residue From this information the sequence of the initial oligosaccharide can clearly only be that as shown in FIG. 43 of the accompanying drawings.

EXAMPLE 4

Figure 44:
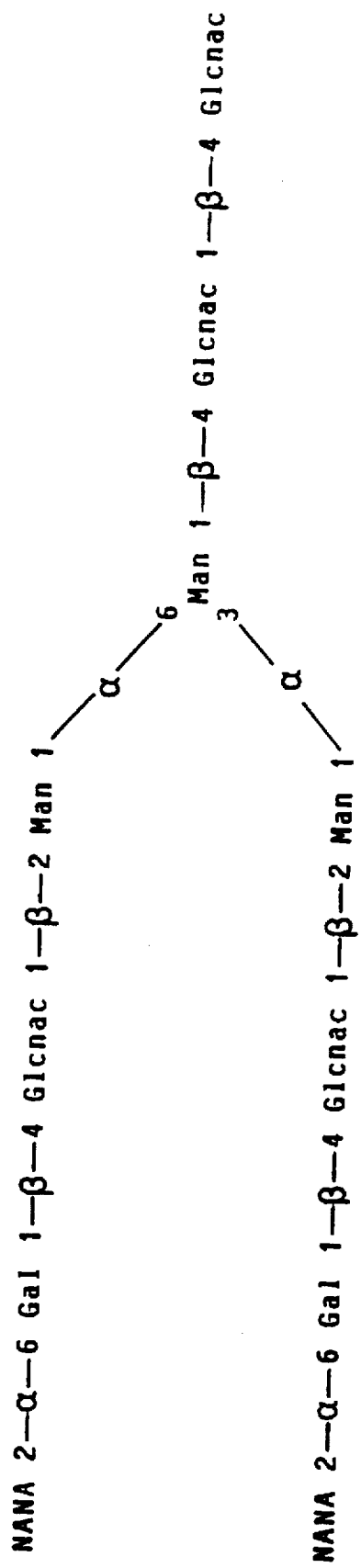
FIG. 44 shows a structure of an oligosaccharide entity to which reference is made in Example 4.

In this Example an oligosaccharide entity comprising an oligosaccharide of the structure given in FIG. 44 of the accompanying drawings was used to demonstrate the use of the present invention.

TABLE 3

| Order of Use of Exoglycosidase | Exoglycosidase Used | Exoglycosidase Reaction Condition (all in 100 μl reaction volume) | Monosaccharide Detected | Nanomoles of Monosaccharide Detected |
|---|---|---|---|---|
| 1 | α-D-mannosidase (jack bean) | 1.4 units in 0.1M sodium acetate/0.01M zinc acetate, pH 5.0 | mannose | 157 |
| 2 | β-N-acetyl-D-hexosaminidase | 48 μunits in 0.1M sodium cacodylate, pH | N-acetyl glucosamine | 141 |

TABLE 3-continued

| Order of Use of Exoglycosidase | Exoglycosidase Used | Exoglycosidase Reaction Condition (all in 100 μl reaction volume) | Monosaccharide Detected | Nanomoles of Monosaccharide Detected |
|---|---|---|---|---|
| | (Streptococcus pneumoniae) | 6.0 | | |
| 3 | α-D-mannosidase (jack bean) | 6 units in 0.1M sodium acetate/0.01M zinc acetate, pH 5.0 | mannose | 145 |
| 4 | β-D-mannosidase (Helix pomatia) | 0.3 units in 0.1M sodium acetate, pH 4.0 | mannose | 151 |
| 5 | β-N-acetyl-D-hexosaminidase (jack bean) | 2.5 units in 0.1M sodium citrate phosphate, pH 4.5 | N-acetyl glucosamine | 142 |

A preliminary analysis of the oligosaccharide was carried out and the following monosaccharide units were identified: NANA (sialic acid) (2 units), Gal (2 units), Glcnac (4 units), Man (3 units).

The oligosaccharide (0.4 mg) was attached to a support material as disclosed in relation to Example 1 to give a conjugated material.

The results of the preliminary analysis were used, in conjunction with a means for selecting a sequencing agent to be applied to an oligosaccharide entity (said means including a logic unit), to identify candidate structures and to select a sequencing agent to be applied to the conjugated material.

The conjugated material was subjected to successive treatments with various sequencing agents (in this Example exoglycosidase enzymes), the choice of each successive sequencing agent being based upon the results of analysis and use of a means for selecting a sequencing agent to be applied to an oligosaccharide entity (said means including a logic unit); the procedures used in this Example were substantially similar to those disclosed in relation to Example 1.

The order in which the various sequencing agents (exoglycosidases in this Example) were applied and the results are set out in Table 4.

The order and ratio of monosaccharides released was as follows:

D-NANA α2→6: 2 residues
D-galactose β1→4: 2 residues
N-acetyl-D-glucosamine β1→2: 2 residues
Mannose α1→6,3: 2 residues
Mannose β1→4: 1 residue
N-acetyl-D-glucosamine β1→4: 1 residue From this information the sequence of the initial oligosaccharide can clearly only be that as shown in FIG. 44 of the accompanying drawings.

We claim:

1. A process for sequencing a primary oligosaccharide compound which is an oligosaccharide or has an oligosaccharide portion, which comprises:

(a) making a first analysis to determine a monosaccharide composition of said primary oligosaccharide compound; and (b) selecting at least one first sequencing agent based on said first analysis; and then (c) applying said at least one first selected sequencing agent to said primary oligosaccharide compound, to give products comprising a residual oligosaccharide compound and at least one monosaccharide released by said at least one first selected sequencing agent;

TABLE 4

| Order of Use of Exoglycosidase | Exoglycosidase Used | Exoglycosidase Reaction Condition (all in 100 μl reaction volume) | Monosaccharide Detected | Nanomoles of Monosaccharide Detected |
|---|---|---|---|---|
| 1 | α-D-neuraminidase (Arthrobacter ureafaciens) | 0.1 unit in 0.1M sodium acetate, pH 5.0 | NANA | 194 |
| 2 | β-D-galactosidase (jack bean) | 1 unit in 0.1M sodium citrate/phosphate, pH 3.5 | Galactose | 176 |
| 3 | β-N-acetyl-D-hexosaminidase (Streptococcus pneumoniae) | 48 μunits in 0.1M sodium cacodylate, pH 6.0 | N-acetyl glucosamine | 187 |
| 4 | α-D-mannosidase (jack bean) | 6 units in 0.1M sodium acetate/0.01M zinc acetate, pH 5.0 | mannose | 201 |
| 5 | β-D-mannosidase (Helix pomatia) | 0.3 units in 0.1M sodium acetate, pH 4.0 | mannose | 90 |
| 6 | β-N-acetyl-D-hexosaminidase (jack bean) | 2.5 units in 0.1M sodium citrate phosphate, pH 4.5 | N-acetyl glucosamine | 83 |

(d) making a second analysis of said at least one monosaccharide in relation to said monosaccharide composition and thereby selecting, based on said second analysis, at least one second sequencing agent for reaction with said residual oligosaccharide compound.

2. A process as claimed in claim 1, comprising repeating steps (c) and (d) until a desired degree of sequencing of said primary oligosaccharide compound has occurred.

3. A process as claimed in claim 1, wherein the process includes the use of a support material upon which said primary oligosaccharide compound to be subjected to sequencing is immobilized.

4. A process as claimed in claim 3 wherein the support material is a solid support material comprising 1,1' carbonyldiimidazole activated agarose.

5. A process as claimed in claim 1, wherein said primary oligosaccharide compound is in free solution.

6. A process as claimed in claim 1, wherein at least one said selected sequencing agent is a chemical agent.

7. A process as claimed in claim 6, wherein said chemical sequencing agent is an enzyme comprising an exoglycosidase or an endoglycosidase.

8. A process as claimed in claim 7 wherein the enzyme is achatina fulica beta mannosidase, a.saitoi alpha mannosidase, jack bean alpha mannosidase, bovine testis beta galactosidase, jack bean beta galactosidase, c.lampas beta xylosidase, s.pneum beta N-acetyl hexosaminidase, jack bean beta n-acetyl hexosaminidase, bovine epididymis alpha fucosidase, c.lampas alpha fucosidase, coffee bean alpha galactosidase, or almond alpha fucosidase.

9. A process as claimed in claim 1, wherein at least one of the at least one first sequencing agent and the at least one second sequencing agent comprises a combination of sequencing agents.

10. A process as claimed in claim 1, further comprising after step (a), preparing a postulated set of possible structures, the postulated set being selected from a set of oligosaccharides having monosaccharides in an amount corresponding to the monosaccharide composition of said primary oligosaccharide compound based on said first analysis.

11. A process as claimed in claim 10, wherein step (b) is further based on said postulated set of possible structures.

* * * * *